(12) United States Patent
Kaminuma et al.

(10) Patent No.: US 8,586,638 B2
(45) Date of Patent: Nov. 19, 2013

(54) PARAKERATOSIS INHIBITOR AND SKIN PREPARATION FOR EXTERNAL USE

(75) Inventors: Mikiko Kaminuma, Yokohama (JP); Masaru Suetsugu, Yokohama (JP); Toshii Iida, Yokohama (JP); Shinji Inomata, Yokohama (JP); Keiko Takada, Yokohama (JP); Yuji Katsuta, Yokohama (JP)

(73) Assignee: Shiseido Company, Ltd, Tokyo (JP)

( * ) Notice: Subject to any disclaimer, the term of this patent is extended or adjusted under 35 U.S.C. 154(b) by 1598 days.

(21) Appl. No.: 10/580,471

(22) PCT Filed: Nov. 22, 2004

(86) PCT No.: PCT/JP2004/017356
§ 371 (c)(1),
(2), (4) Date: Feb. 22, 2007

(87) PCT Pub. No.: WO2005/051340
PCT Pub. Date: Jun. 9, 2005

(65) Prior Publication Data
US 2007/0225380 A1   Sep. 27, 2007

(30) Foreign Application Priority Data

Nov. 27, 2003  (JP) .................... 2003-397299
Nov. 27, 2003  (JP) .................... 2003-397307

(51) Int. Cl.
*A61K 47/12*  (2006.01)
(52) U.S. Cl.
USPC ........................................................ 514/785
(58) Field of Classification Search
USPC ........................................................ 514/785
See application file for complete search history.

(56) References Cited

U.S. PATENT DOCUMENTS

| | | | |
|---|---|---|---|
| 4,169,550 A | 10/1979 | Williams | |
| 4,246,194 A | 1/1981 | Ferguson | |
| 5,869,068 A | 2/1999 | De Lacharriere et al. | |
| 6,824,786 B2 * | 11/2004 | Yu et al. | 424/401 |
| 2005/0152930 A1 * | 7/2005 | Katsuta et al. | 424/401 |

FOREIGN PATENT DOCUMENTS

| | | |
|---|---|---|
| JP | 3-223206 | 10/1991 |
| JP | 5-097627 | 4/1993 |
| JP | 5-105619 | 4/1993 |

(Continued)

OTHER PUBLICATIONS

Kyowa "cosmetics containing . . . " CA79:22615a (1973).*

(Continued)

*Primary Examiner* — Celia Chang
(74) *Attorney, Agent, or Firm* — Turocy & Watson, LLP

(57) ABSTRACT

To provide a parakeratosis inhibitor, pore reducing agent and skin roughness preventing/ameliorating agent that exhibit capabilities of parakeratosis inhibition, pore reduction, skin roughness prevention/amelioration, etc., and further provide a skin preparation for external use having these capabilities. There are provide a parakeratosis inhibitor and a pore reducing agent each comprising at least one compound selected from the group consisting of a glycine derivative, an aminodicarboxylic acid derivative, an acylaminodicarboxylic acid derivative, a pyrrolidinecarboxylic acid derivative, a piperidinecarboxylic acid derivative, a hexamethyleneiminecarboxylic acid, a beta-alanine derivative and salts of these derivatives. Further, there are provided a parakeratosis inhibitor, a pore reducing agent and a skin roughness preventing/ameliorating agent each comprising at least one compound selected from the group consisting of specified glycine derivatives and salts thereof and specified aminosulfuric acid derivatives and salts thereof. Still further, there are provided skin preparations for external use comprising these compounds.

3 Claims, 2 Drawing Sheets

Effect on pores (total surface area)

(56) References Cited

FOREIGN PATENT DOCUMENTS

| | | | |
|---|---|---|---|
| JP | 5-117136 | | 5/1993 |
| JP | 10-175844 | | 6/1998 |
| JP | 11-130650 | | 5/1999 |
| JP | 11-139951 | | 5/1999 |
| JP | 11-158055 | * | 6/1999 |
| JP | 2000-178118 | | 6/2000 |
| JP | 2002-080359 | | 3/2002 |
| JP | 2002-2412260 | | 8/2002 |
| JP | 2002-534369 | | 10/2002 |
| JP | 2002-338426 | | 11/2002 |
| JP | 2003-342195 | | 12/2003 |
| JP | 2004-123554 | | 4/2004 |
| JP | 2005-145925 | | 6/2005 |
| WO | 00-51561 | | 9/2000 |
| WO | 02/083136 | | 10/2002 |
| WO | WO 03/099327 | | 12/2003 |
| WO | WO03099327 | * | 12/2003 |

OTHER PUBLICATIONS

Kyowa "consmetics containing . . . " CA93:210106 (1980).*
Ueno et al. "Skin preparation . . . " CA131:35667 (1999).*
Kitano et al. "Cosmetics containing . . . " CA134:285482 (2001).*
Okuri et al., *Japan Society of Dermatology Annual Meeting Program/Abstract*, Mar. 3, 2004, p. 601, vol. 114, No. 3.
Iida et al., *102nd Annual Meeting Programs and Abstract*, Apr. 2003, p. 846, vol. 113, No. 5.
Yazawa et al., *Fragrance Journal*, Feb. 2002, pp. 54-58, vol. 30, No. 2.
Good, Norman et al., "Hydrogen Ion Buffers for Biological Research," *Biochemistry*, Feb. 2006, pp. 467-0477, vol. 5, No. 2.
Taiwanese Office Action for U.S. Appl. No. 10/580,471 corresponding to PCT/JP2004/017356 Issued on Nov. 17, 2010.

* cited by examiner

Effect on parakeratosis (at 4 weeks after application)

Effect on pores (total surface area)

PARAKERATOSIS INHIBITOR AND SKIN PREPARATION FOR EXTERNAL USE

TECHNICAL FIELD

The invention relates to a parakeratosis inhibitor that inhibits parakeratosis caused by sebum, a pore-shrinking agent that maintains normal skin conditions around the pore and suppresses a conical structure of the pore from becoming conspicuous by inhibiting parakeratosis caused by stimulatory components in the sebum around the pore, a skin roughness preventing/ameliorating agent that prevents/ameliorates the skin roughness caused by unsaturated fatty acids, and skin preparation for external use that exhibits capabilities of parakeratosis inhibition, pore shrinkage, skin roughness prevention/amelioration, etc.

BACKGROUND ART

Recently, many people, young ladies among others, have worried about conspicuous pores and have demanded a skin preparation for external use for making the pore inconspicuous. However, the mechanism for making the pore conspicuous has not been elucidated yet, and use of an astringent lotion and excision of parakeratosis have been usual treatments of parakeratosis. Or the skin problem has been often covered apparently by means of foundation cream. The astringent lotion is used to tighten the skin, and the action thereof is to temporarily reduce the temperature of the skin surface with alcohol, or to coagulate proteins with organic acids and the like. Accordingly, the skin suffers a great burden since the skin is temporarily tightened without fundamentally solving the problem of conspicuous pores, and the effect of the astringent lotion has been insufficient.

On the other hand, it has been reported that the derivatives of glycolic acid and ascorbic acid have the effect of pore shrinking (see, for example non-patent reference #1). The mechanism of action and the extent of effect thereof are still unknown.

Excision of keratin plug is to physically remove the keratin plug. Some known methods of excision include parakeratosis remover containing a high molecular weight compound having salt-generating groups (see, for example, patent reference #1), cosmetics containing water-insoluble cyclodextrin polymers (see, for example, patent reference #2), keratin plug remover cosmetics containing not less than 50 weight % of oil having a coefficient of viscosity of 5 to 80 mPa·s/25 degrees centigrade (see, for example, patent reference #3). Physical removal of the keratin plug may damage the skin by a physical force, and side effects on the skin have been a problem. The effect of this method is not always satisfactory since the effect thereof is temporary and keratin plug is readily regenerated, and removal of keratin plug may only expand the pore.

The inventors of the present invention have made intensive studies on the mechanism of generating the conspicuous pores in order to develop a skin preparation for external use that exhibits capabilities of ameliorating the conspicuous pores, and found and reported at the $102^{nd}$ annual meeting of Japan Society of Dermatology (see non-patent reference #2) that:

(1) the conically recessed portion around the pore is recognized as pore, and the pores become conspicuous if this portion is wider;

(2) the skin surface stratum corneum of the conical portion is in a state of parakeratosis (there remains nucleus which should have disappeared);

(3) those person having conspicuous pore excretes a lot of sebum, in particular unsaturated fatty acids;

(4) the unsaturated fatty acids cause the parakeratosis; and (5) the conspicuous pore is likely to be caused by the unsaturated fatty acids contained in the sebum.

The inventors of the present invention have elucidated that the mechanism of developing conspicuous pore may be partly due to parakeratosis caused by the sebum. The inventors have also elucidated that the amelioration of parakeratosis may lead to the amelioration of conspicuous pores.

Patent reference #1: JP-A-H05-97627
Patent reference #2: JP-A-H05-105619
Patent reference #3: JP-A-2002-241260
Non-patent reference #1: Yazawa, et al., Fragrance Journal, 2002, vol. 30, No. 2, pp. 54-58
Non-patent reference #2: Iida, et al., $102^{nd}$ annual meeting programs and abstract, 2003, 103, pp. 846

DISCLOSURE OF THE INVENTION

The present invention has been made in view of above circumstances and has an object of providing a new parakeratosis inhibitor agent that exhibits the capabilities of parakeratosis inhibition, pore-shrinking, skin roughness prevention/amelioration, etc., a pore shrinking agent, a skin roughness prevention/amelioration agent, and a further object of providing a skin preparation for external use having these capabilities.

In order to solve the above problem, the inventors of the present invention conducted research, based on the above knowledge, on compounds having a parakeratosis inhibitory function caused by the unsaturated fatty acids, and found that some specific aminocarbonic acid derivatives, such as glycine derivatives, and salts thereof, and some specific aminosulfuric acid derivatives and salts thereof have the capabilities mentioned above. The invention has been completed based on these discoveries.

More specifically, the present invention provides a parakeratosis inhibitor agent and pore-shrinking agent comprising at least one, two or more compounds selected from a group consisting of a glycine derivative, an aminodicarboxylic acid derivative, an acylaminodicarboxylic acid derivative, a pyrrolidinecarboxylic acid derivative, a piperidinecarboxylic acid derivative, a hexamethyleneiminecarboxylic acid, a beta-alanine derivative and salts of these derivatives.

Said glycine derivative is preferably the glycine derivative as represented by the following general formula (1):

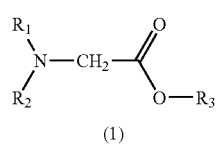

[formula 11]

(1)

(In the above formula (1), $R_1$ and $R_2$ each represent respectively and independently a hydrogen atom, an alkyl group, an alkenyl group, an aryl group, an aralkyl group, an aminomethylcarbonyl group, an amidino group, an alkyl-carbonyl group, an alkenyl-carbonyl group, an aryl-carbonyl group, or an aralkyl-carbonyl group; $R_3$ represents a hydrogen atom, an alkyl group, an alkenyl group, an aryl group, or an aralkyl group. It should be noted that all of $R_1$, $R_2$, and $R_3$ may not be hydrogen atoms at the same time.)

Said amino-dicarbonic acid derivative is preferably a benzoylaminodicarbonic acid derivative or a benzene sulfonylaminodicarbonic acid derivative as represented by the following general formula (2):

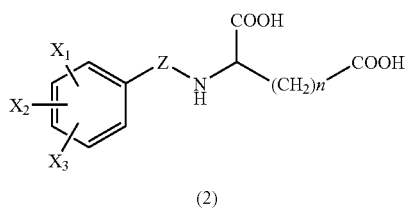

[formula 12]

(2)

(In the above formula (2), $X_1$, $X_2$, and $X_3$ each represent respectively and independently a hydrogen atom, an alkyl group having 1 to 4 carbons, an alkoxyl group having 1 to 4 carbons, a hydroxyl group, an amino group, an alkylamino group having 1 to 4 carbons, a chlorine atom, a bromine atom, a fluorine atom, iodine atom, or a trifluoromethyl group, and Z represents a carbonyl group or a sulfonyl group, where n is 1 or 2.)

Said acylaminodicarbonic acid derivative is preferably an acylaminodicarbonic acid derivative as represented by the following general formula (3):

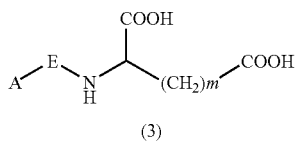

[formula 13]

(3)

(In the above formula (3), A represents an alkyl group or an alkenyl group having 1 to 18 carbons, E represents a carbonyl group or a sulfonyl group, where m is 1 or 2.)

Said pyrrolidinecarboxylic acid derivative, said piperidinecarboxylic acid derivative, and said hexamethyleneiminecarboxylic acid derivative are preferably a pyrrolidine carboxylic acid derivative, a piperidinecarboxylic acid derivative, and a hexamethyleneiminecarboxylic acid derivative as represented by the following general formula (4):

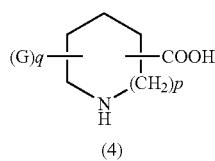

[formula 14]

(4)

(In the above formula (4), G represents an alkyl group having 1 to 4 carbons, an alkoxyl group having 1 to 4 carbons, a hydroxyl group, an amino group, an alkylamino group having 1 to 4 carbons, a chlorine atom, a bromine atom, a fluorine atom, an iodine atom, or a trifluoromethyl group, and q is 0, 1, 2, or 3. p is 0, 1, or 2.)

Said beta-alanine derivative is preferably a beta-alanine derivative as represented by the following general formula (5):

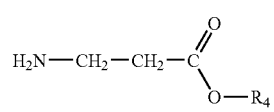

[formula 15]

(5)

(In the above formula (5), $R_4$ represents a hydrogen atom, an alkyl group, an alkenyl group, an aryl group, or an aralkyl group.)

In addition, the present invention provides a parakeratosis inhibitor agent and pore-shrinking agent comprising as effective ingredients at least one, two or more compounds selected from a group consisting of said glycine derivative, aminodicarboxylic acid derivative, acylaminodicarboxylic acid derivative, pyrrolidine carboxylic acid derivative, piperidinecarboxylic acid derivative, hexamethyleneiminecarboxylic acid, beta-alanine derivative and said salts of these derivatives.

In addition, the present invention provides a parakeratosis inhibitory skin preparation for external use containing said parakeratosis inhibitor agent.

In addition, the present invention provides a pore-shrinking skin preparation for external use containing said pore-shrinking agent.

Herein the invention with respect to the above compounds including said glycine derivative, aminodicarboxylic acid derivative, acylaminodicarboxylic acid derivative, pyrrolidine carboxylic acid derivative, piperidinecarboxylic acid derivative, hexamethyleneiminecarboxylic acid, beta-alanine derivative and said salts of these derivatives will be referred to as invention 1 of the present invention.

In addition, the present invention provides a parakeratosis inhibitor agent, a pore-shrinking agent, and a skin roughness preventing/ameliorating agent, comprising at least one, two or more compounds selected from a group consisting of glycine derivatives and salts thereof represented by the following general formulae (6), (7), or (8), and aminosulfuric acid derivatives and salts thereof represented by the following general formulae (9) and (10).

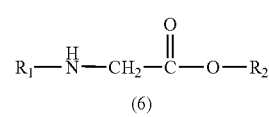

[formula 16]

(6)

(In the above formula (6), $R_1$ represents an alkyl group having 2 to 18 carbons, a phenyl group, a carbamoyl group or a piridylcarbonyl group, $R_2$ represents a hydrogen atom, an alkyl group of straight or branched chain having 1 to 18 carbons, a benzyl group or a phenyl group. The phenyl portion of benzyl group and the phenyl group may also be replaced with one to three alkyl groups each having 1 to 4 carbons, an alkoxyl group having 1 to 4 carbons, a hydroxyl group, or an amino group.)

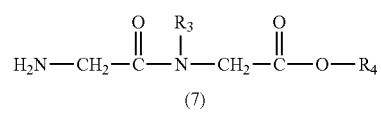

[formula 17]

(7)

(In the above general formula (7), $R_3$ represents a hydrogen atom or a methyl group, $R_4$ represents a hydrogen atom, an alkyl group of straight or branched chain having 1 to 18 carbons, a benzyl group, or a phenyl group. The phenyl portion of benzyl group and the phenyl group may be replaced with an alkyl group having 1 to 4 carbons, an alkoxyl group having 1 to 4 carbons, a hydroxyl group or an amino group. However when $R_3$ is a hydrogen atom, $R_4$ should not be a hydrogen atom.)

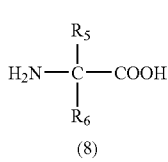

[formula 18]

(8)

(In the above general formula (8), $R_5$ and $R_6$ represent respectively independently an alkyl group having 1 to 4 carbons, and $R_5$ together with $R_6$ may also form a cycloalkyl group having 4 to 7 carbons.)

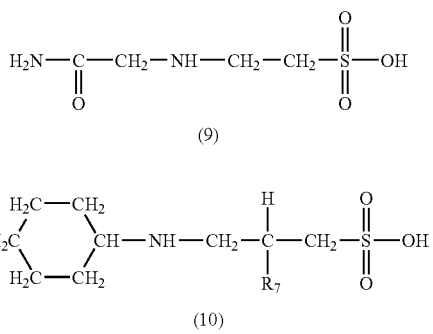

[formula 19]

(9)

[formula 20]

(10)

(In the above general formula (10), $R_7$ represents a hydrogen atom or a hydroxyl group.)

The present invention provides a parakeratosis inhibitor agent, a pore-shrinking agent, and a skin roughness preventing/ameliorating agent having as effective ingredients at least one, two or more compounds selected from a group consisting of the glycine derivatives and the salts thereof represented by the above formulae (6), (7), or (8), as well as the aminosulfuric acid derivatives and the salts thereof represented by the above formulae (9) and (10).

The present invention provides a skin preparation for external use containing at least one, two or more compounds selected from a group consisting of the glycine derivatives and the salts of these derivatives represented by the above formulae (6), (7), or (8) and the aminosulfuric acid derivatives and the salts thereof represented by the above formulae (9) and (10).

Herein the invention with respect to the above compounds including said glycine derivatives and the salts of these derivatives represented by said general formulae (6), (7), or (8) as well as the aminosulfuric acid derivatives and the salts of these derivatives represented by the above formulae (9) or (10) will be referred to as invention 2 in accordance with the present invention.

It is preferable for the parakeratosis inhibitor agent, the pore-shrinking agent, and the skin roughness preventing/ameliorating agent in accordance with said invention 2 that the $R_2$ in the above formula (6) is a hydrogen atom.

It is preferable for the parakeratosis inhibitor agent, the pore-shrinking agent, and the skin roughness preventing/ameliorating agent in accordance with said invention 2 that the $R_1$ in the above formula (6) is a carbamoyl group and $R_2$ is a hydrogen atom.

It is preferable for the parakeratosis inhibitor agent, the pore-shrinking agent, and the skin roughness preventing/ameliorating agent in accordance with said invention 2 that the $R_1$ in the above formula (6) is a phenyl group and $R_2$ is a hydrogen atom.

It is preferable for the parakeratosis inhibitor agent, the pore-shrinking agent, and the skin roughness preventing/ameliorating agent in accordance with said invention 2 that the $R_1$ in said general formula (6) is an ethyl group, and $R_2$ is a hydrogen atom.

It is preferable for the parakeratosis inhibitor agent, the pore-shrinking agent, and the skin roughness preventing/ameliorating agent in accordance with said invention 2 that the $R_1$ in said general formula (6) is a nicotinoyl group, and $R_2$ is a hydrogen atom.

It is preferable for the parakeratosis inhibitor agent, the pore-shrinking agent, and the skin roughness preventing/ameliorating agent in accordance with said invention 2 that the $R_3$ in said general formula (7) is a methyl group.

It is preferable for the parakeratosis inhibitor agent, the pore-shrinking agent, and the skin roughness preventing/ameliorating agent in accordance with said invention 2 that the $R_5$ and $R_6$ in said general formula (8) are both a cyclopentamethylene group.

It is preferable for the skin preparation for external use in accordance with the invention 2 that $R_2$ in said general formula (6) is a hydrogen atom.

It is preferable for the skin preparation for external use in accordance with the invention 2 that $R_1$ in said general formula (6) is a carbamoyl group, and $R_2$ is a hydrogen atom.

It is preferable for the skin preparation for external use in accordance with the invention 2 that $R_1$ in said general formula (6) is a phenyl group, and $R_2$ is a hydrogen atom.

It is preferable for the skin preparation for external use in accordance with the invention 2 that $R_1$ in said general formula (6) is an ethyl group, and $R_2$ is a hydrogen atom.

It is preferable for the skin preparation for external use in accordance with the invention 2 that $R_1$ in said general formula (6) is a nicotinoyl group, and $R_2$ is a hydrogen atom.

It is preferable for the skin preparation for external use in accordance with the invention 2 that $R_3$ in said general formula (7) is a methyl group.

It is preferable for the skin preparation for external use in accordance with the invention 2 that $R_5$ and $R_6$ in said general formula (8) are both a cyclopentamethylene groups.

In accordance with the present invention, a parakeratosis inhibitor agent for inhibiting the parakeratosis caused by the sebum, a pore-shrinking agent for inhibiting the parakeratosis caused by the stimulatory component in the sebum around the pores, for keeping skin healthy around the pores, and for inhibiting the conspicuous conical pore structure, and a skin roughness preventing/ameliorating agent for preventing and ameliorating the skin roughness caused by the unsaturated fatty acids are provided. A skin preparation for external use that has the capabilities of parakeratosis inhibition, pore reduction, and skin roughness prevention/amelioration is also provided.

BEST MODE FOR CARRYING OUT THE INVENTION

The present invention will be described in greater details herein below.

The invention 1 in accordance with the present invention uses a glycine derivative, an aminodicarboxylic acid derivative, an acylaminodicarboxylic acid derivative, a pyrrolidine carboxylic acid derivative, a piperidinecarboxylic acid derivative, a hexamethyleneiminecarboxylic acid, a beta-alanine derivative and salts of these derivatives.

Preferably the glycine derivative in accordance with the invention 1 is that represented by the following formula (1):

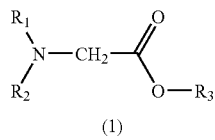

[formula 21]

(1)

In the invention 1, at least one, two or more compounds selected from said glycine derivatives.

$R_1$ and $R_2$ in the general formula (1) are respectively and independently a hydrogen atom, an alkyl group, an alkenyl group, an aryl group, an aralkenyl group, an aminomethylcarbonyl group, an amidino group, an alkyl-carbonyl group, an alkenyl-carbonyl group, an aryl-carbonyl group, or an aralkyl-carbonyl group. Preferably either one of $R_1$ or $R_2$ in the general formula (1) is a hydrogen atom, the other is a methyl group, an aminomethylcarbonyl group, or a benzylcarbonyl group.

$R_3$ in the general formula (1) is a hydrogen atom, an alkyl group, an alkenyl group, an aryl group, or an aralkyl group. $R_3$ in the general formula (1) is preferably a hydrogen atom or an alkyl group, and said alkyl group is preferably a methyl group, an ethyl group, an n-butyl group, or a t-butyl group. In particular, $R_3$ in the general formula (1) is more preferably a hydrogen atom or an ethyl group. It should be noted that $R_1$, $R_2$, and $R_3$ in the general formula (1) might not be all hydrogen atoms at the same time. In addition, $R_1$ and $R_2$ in the general formula (1) is more preferably a glycine ester, which is a hydrogen atom, and most preferably an alkyl ester having 1 to 4 carbons or a benzyl ester.

Some specific examples of the glycine derivatives and the salt of the derivatives as represented by the general formula (1) includes, for example, sarcosine (N-methylglycine), N-ethylglycine, N-propylglycine, N-diethylglycine, N-dimethylglycine, N-amidinoglycine, N-amidino-N-methylglycine, glycylglycine, phenaceturic acid, glycine methyl ester hydrochloride, glycine ethyl ester hydrochloride, glycine n-butyl ester hydrochloride, glycine t-butyl ester hydrochloride, glycine n-propyl ester hydrochloride, glycine n-pentyl ester hydrochloride, and glycine benzyl ester hydrochloride.

Among others, sarcosine, glycylglycine, phenaceturic acid, glycine ethyl ester hydrochloride, glycine benzyl ester hydrochloride are preferable, and sarcosine, glycylglycine, phenaceturic acid are most preferable.

The preferable aminodicarbonic acid derivatives in accordance with the invention 1 are a benzoylaminodicarbonic acid derivative or a benzene sulfonylaminodicarbonic acid derivative as represented by the following formula (2):

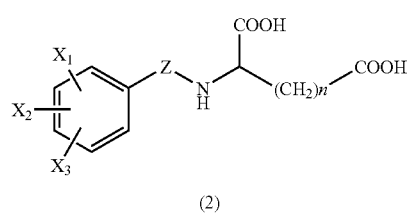

[formula 22]

(2)

In the invention 1, at least one or two or more compounds selected from said aminodicarbonic acid derivatives.

$X_1$, $X_2$, and $X_3$ in the general formula (2) may be respectively and independently a hydrogen atom, an alkyl group having 1 to 4 carbons, an alkoxyl group having 1 to 4 carbons, a hydroxyl group, an amino group, an alkylamino group having 1 to 4 carbons, a chlorine atom, a bromine atom, a fluorine atom, an iodine atom, or a trifluoromethyl group. Z in the general formula (2) may be a carbonyl group or a sulfonyl group, and n in the general formula (2) is 1 or 2. It is preferable that $X_1$, $X_2$, and $X_3$ in the general formula (2) are hydrogen atoms. A glutamate derivative with n=2 in the general formula (2) is preferable.

Some specific examples of benzoylaminodicarbonic acid derivatives and benzene sulfonylaminodicarbonic acid derivatives as well as the salts of these derivatives as represented by the general formula (2) include, for example, N-benzoyl-L-glutamic acid, N-benzene-sulfonyl-L-glutamic acid, N-benzoyl-D-glutamic acid, N-benzene-sulfonyl-D-glutamic acid, N-(p-methoxybenzoyl)-L-glutamic acid, N-(p-methoxybenzenesulfonyl)-L-glutamic acid, N-benzoyl-L-aspartic acid, N-benzene-sulfonyl-L-aspartic acid, N-benzoyl-D-aspartic acid, and N-benzene-sulfonyl-D-aspartic acid.

Among these, N-benzoyl-L-glutamic acid, and N-benzene-sulfonyl-L-glutamic acid are preferable.

For the acylaminodicarbonic acid derivatives in accordance with the invention 1, acylaminodicarbonic acid derivatives as represented by the following general formula (3) are preferable:

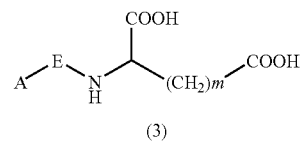

[formula 23]

(3)

The invention 1 uses at least one or two or more compounds selected from said acylaminodicarbonic acid derivatives.

A in the general formula (3) is an alkyl group or an alkenyl group having 1 to 18 carbons, where an alkyl group having 1 to 3 carbons is preferable, and a methyl group is most preferable. E in the general formula (3) is a carbonyl group or a sulfonyl group, and a carbonyl group is preferable. m in the general formula (3) is 1 or 2.

Some specific examples of the acylaminodicarbonic acid derivatives and the salts thereof represented by the general formula (3) include, N-acetyl-L-aspartic acid, N-acetyl-L-glutamic acid, N-acetyl-D-aspartic acid, N-acetyl-D-glutamic Acid, N-ethyl-sulfonyl-L-aspartic acid, N-ethyl-sulfonyl-D-aspartic acid, N-methyl-sulfonyl-D-aspartic acid, N-methyl-sulfonyl-L-aspartic acid, N-methyl-sulfonyl-D-glutamic acid, and N-methyl-sulfonyl-L-glutamic acid.

Among those cited above, N-acetyl-L-glutamic acid, and N-acetyl-L-aspartic acid are preferable.

For the pyrrolidine carboxylic acid derivative, piperidinecarboxylic acid derivative, and hexamethyleneiminecarboxylic acid in accordance with said invention 1, a pyrrolidine carboxylic acid derivative, a piperidinecarboxylic acid derivative, and a hexamethyleneiminecarboxylic acid derivative as represented by the following general formula (4) are preferable.

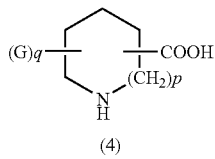

[formula 24]

(4)

The invention 1 uses at least one or two or more compounds selected from said pyrrolidine carboxylic acid derivative, piperidinecarboxylic acid derivative, and hexamethyleneiminecarboxylic acid derivative.

G in the general formula (4) is an alkyl group having 1 to 4 carbons, an alkoxyl group having 1 to 4 carbons, a hydroxyl group, an amino group, an alkylamino group having 1 to 4 carbons, a chlorine atom, a bromine atom, a fluorine atom, an iodine atom or a trifluoromethyl group. In the general formula (4) q is 0, 1, 2, or 3. p in the general formula (4) is 0, 1, or 2.

Some specific examples of the pyrrolidine carboxylic acid derivative, piperidinecarboxylic acid derivative, and hexamethyleneiminecarboxylic acid derivative and the salts of these derivatives as represented by the general formula (4) include, for example, L-proline, hydroxy-L-proline, nipecotic acid, isonipecotic acid, and pipecolic acid.

For the beta-alanine derivative in accordance with said invention 1, beta-alanine derivatives as represented by the general formula (5) are preferable.

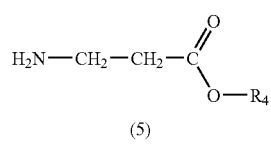

[formula 25]

(5)

The invention 1 uses at least one or two or more compounds selected from said beta-alanine derivatives.

$R_4$ in the general formula (5) is a hydrogen atom, an alkyl group, an alkenyl group, an aryl group, or an aralkyl group. For this $R_4$ a hydrogen atom or an alkyl group is preferable, and for said alkyl group a methyl group, an ethyl group, a t-butyl group, an n-butyl group are preferable.

Some specific examples of the beta-alanine derivative and the salts of the derivative as represented by general formula (5) include, for example, beta-alanine, beta-alanine methyl-ester hydrochloride, beta-alanine ethyl-ester hydrochloride, and beta-alanine n-hexyl-ester hydrochloride.

Among these, beta-alanine and beta-alanine ethyl-ester hydrochloride are preferable.

Some specific salts used for the formation of salt compounds of said glycine derivatives, aminodicarbonic acid derivatives, acylaminodicarbonic acid derivatives, pyrrolidinecarbonic acid derivatives, piperidinecarbonic acid derivatives, hexamethyleneiminecarbonic acid derivatives and beta-alanine derivatives include, for example, some inorganic salts, which include hydrochloride salts, sulfate salts, phosphate salts, hydrobromide salts, sodium salts, potassium salts, magnesium salts, calcium salts, and ammonium salts, and some organic salts, which include acetate salts, lactate salts, maleate salts, fumarate salts, tartrate salts, citrate salts, methane-sulfonic acid salts, p-toluene-sulfonic acid salts, triethanolamine salts, diethanolamine salts, and amino acid salts, but are not limited thereto. Said salt compounds used in the invention 1 can be prepared in accordance with well-known preparation.

The glycine derivatives, aminodicarbonic acid derivatives, acylaminodicarbonic acid derivatives, pyrrolidinecarbonic acid derivatives, piperidinecarbonic acid derivatives, hexamethyleneiminecarbonic acid derivatives, and beta-alanine derivatives, as well as the salts of said derivatives in accordance with the invention 1 are for example commercially marketed and readily available as reagents. These can be synthesized in accordance with well-known preparation methods as well.

Said glycine derivatives, aminodicarbonic acid derivatives, acylaminodicarbonic acid derivatives, pyrrolidinecarbonic acid derivatives, piperidinecarbonic acid derivatives, hexamethyleneiminecarbonic acid derivatives and beta-alanine derivatives and the salts of said derivatives in accordance with the invention 1 will have excellent capabilities of inhibiting parakeratosis, and of reducing the pores, as will be proven herein below. At least one or two or more compounds selected from a group consisting of glycine derivatives, aminodicarbonic acid derivatives, acylaminodicarbonic acid derivatives, pyrrolidinecarbonic acid derivatives, piperidinecarbonic acid derivatives, hexamethyleneiminecarbonic acid derivatives and beta-alanine derivatives and the salts of said derivatives in accordance with the invention 1 (hereinafter, at least one or two or more compounds selected from a group consisting of the glycine derivatives, aminodicarbonic acid derivatives, acylaminodicarbonic acid derivatives, pyrrolidinecarbonic acid derivatives, piperidinecarbonic acid derivatives, hexamethyleneiminecarbonic acid derivatives and beta-alanine derivatives and the salts of said derivatives in accordance with the invention 1 will be referred to as "aminocarbonic acid derivatives") are useful for the parakeratosis inhibitor agent and the pore-shrinking agent.

The parakeratosis inhibitor agent and the pore-shrinking agent containing as effective ingredient said aminocarbonic acid derivatives are also useful. The composition of the parakeratosis inhibitor agent and the pore-shrinking agent is preferably applied in the form of skin preparation for external use to, for example, ameliorate the conspicuous pores of the nose and cheeks as facial use, and ameliorate the conspicuous pores after leg epilation as body use.

The parakeratosis inhibitor agent and the pore-shrinking agent in accordance with the invention 1 are novel and useful application based on the discovery of said novel capabilities of said aminocarbonic acid derivatives.

Said parakeratosis inhibitor agent and the pore-shrinking agent in accordance with the invention 1 has a vast usage range of application, and may be applied in a variety of fields. Said fields include, for example, cosmetics including medicated cosmetics, medicines, and foods, and these are preferable.

The parakeratosis inhibitor agent and the pore-shrinking agent in accordance with the invention 1 may be blended with a skin preparation for external use as the parakeratosis inhibitor component, or the pore-shrinking component to prepare as a skin preparation for external use for the parakeratosis inhibition or a skin preparation for external use for the pore reduction.

The skin preparation for external use containing said parakeratosis inhibitor agent or pore-shrinking agent in accordance with the invention 1 will be useful as a skin preparation for external use for parakeratosis inhibition which exhibits the parakeratosis inhibition effect, and as a skin preparation for external use for pore shrinkage which exhibits the pore shrinking effect (the skin preparation for external use for the parakeratosis inhibition and the skin preparation for external use for the pore shrinkage will be collectively referred to as "functional skin preparation for external use" hereinafter).

Said functional skin preparation for external use in accordance with the invention 1 may be preferably used to a pore-shrinking agent, a facial cosmetics that ameliorates the conspicuous pores of the nose and cheeks, a skin preparation for external use that ameliorates the conspicuous pores of legs after epilation.

When said parakeratosis inhibitor agent or the pore-shrinking agent in accordance with the invention 1 is included as an ingredient in a composition such as a parakeratosis inhibition composition, pore-shrinking composition or functional skin preparation for external use, the effective amount of the parakeratosis inhibitor agent or the pore-shrinking agent as said ingredient may be respectively contained for exhibiting their respective functionality, and the effective contained amount is preferably 0.001 to 20.0 weight % of said composition, more preferably 0.01 to 10.0 weight %, and most preferably 0.2 to 5.0 weight %.

The invention 2 of the present invention uses at least one or two or more compounds selected from a group consisting of the glycine derivatives and the salts thereof as represented by the general formulae (6), (7), or (8), and the aminosulfuric acid derivatives and the salts thereof as represented by the general formulae (9) or (10).

The glycine derivatives and the salts thereof as represented by the general formulae (6), (7), or (8) in accordance with the invention 2 will be described now. In the invention 2, at least one or two or more compounds selected from a group consisting of the glycine derivatives and the salts thereof as represented by the following general formulae (6), (7), or (8).

[formula 26]

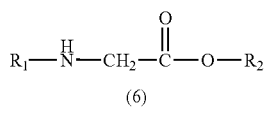

(6)

[formula 27]

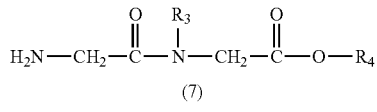

(7)

[formula 28]

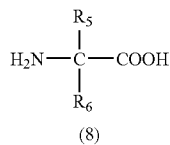

(8)

$R_1$ in said general formula (6) is an alkyl group having 2 to 18 carbons, a phenyl group, a carbamoyl group, or a piridylcarbonyl group. Some examples of the alkyl group having 2 to 18 carbons include, for example, an ethyl group, a propyl group, a butyl group, a pentyl group, a hexyl group, a heptyl group, an octyl group, a decyl group, a dodecyl group, a tetradecyl group, a hexadecyl group, an octadecyl group, and an isopropyl group. The piridylcarbonyl group includes for example a nicotinoyl group. Among these $R_1$, the ethyl group, phenyl group, carbamoyl group, and nicotinoyl group are preferable.

$R_2$ in the general formula (6) is a hydrogen atom, an alkyl group of straight or branched chain having 1 to 18 carbons, a benzyl group, or a phenyl group. The phenyl portion of said benzyl group and the phenyl group may be replaced with one to three groups of an alkyl group having 1 to 4 carbons, an alkoxyl group having 1 to 4 carbons, a hydroxyl group or an amino group. Among these $R_2$, a hydrogen atom and a strait chained alkyl group having 1 to 3 carbons are preferable, the hydrogen atom and the ethyl group are more preferable, and the hydrogen atom is most preferable. The invention 2 uses at least one or two or more compounds selected from a group consisting of the glycine derivatives and the salts thereof as represented by the general formula (6).

$R_3$ in the general formula (7) is a hydrogen atom or a methyl group, and the methyl group is preferable. $R_4$ in the general formula (7) is a hydrogen atom, an alkyl group of straight or branched chain having 1 to 18 carbons, a benzyl group, or a phenyl group. The phenyl portion of benzyl group and the phenyl group in $R_4$ of the general formula (7) may be replaced with one to three alkyl groups having 1 to 4 carbons, an alkoxyl group having 1 to 4 carbons, a hydroxyl group, or an amino group. However, if $R_3$ of the general formula (7) is a hydrogen atom, then $R_4$ of the general formula (7) is not a hydrogen atom. Among those of $R_4$ of the general formula (7), the hydrogen atom, and the straight or branched chain alkyl group having 1 to 4 carbons are preferable, the hydrogen atom and the straight chain alkyl group having 1 to 3 carbons are more preferable, and the hydrogen atom and the ethyl group are most preferable. The invention 2 uses at least one or two or more compounds selected from the glycine derivatives and the salts thereof as represented by the formula (7) above.

$R_5$ and $R_6$ in said general formula (8) are respectively and independently an alkyl group having 1 to 4 carbons, the $R_5$ together with $R_6$ may form a cycloalkyl group having 4 to 7 carbons. The cycloalkyl group includes for example a cyclopentamethylene group. The invention 2 uses at least one or two or more compounds selected from the glycine derivatives and the salts thereof represented by said general formula (8).

Some salts used for the formation of salts of said glycine derivatives in accordance with the invention 2 include, but are not limited to, for example, some inorganic salts such as hydrochloride salts, sulfate salts, phosphate salts, hydrobromide salts, sodium salts, potassium salts, magnesium salts, calcium salts, and ammonium salts, and some organic salts, such as acetate salts, lactate salts, maleate salts, fumarate salts, tartrate salts, citrate salts, methane-sulfonic acid salts, p-toluene-sulfonic acid salts, triethanolamine salts, diethanolamine salts, and amino acid salts. Said salt compounds of the glycine derivatives used in the invention 2 can be prepared in accordance with well known preparation method.

Some specific examples of the glycine derivatives and the salts thereof represented by the general formula (6) include, for example, N-ethylglycine, N-n-propylglycine, N-iso-propylglycine, N-n-hexylglycine, N-phenylglycine, N-phenylglycine ethyl-ester, hydantoic acid, N-nicotinoylglycine, N-nicotinoylglycine ethyl ester, and the salts thereof. Among these, N-ethylglycine, N-phenylglycine, hydantoic acid are preferable.

Some specific examples of the glycine derivatives and the salts thereof represented by the general formula (7) include, for example, glycyl sarcosine, glycylglycine ethyl ester hydrochloride salt, glycyl sarcosine ethyl ester hydrochloride salt, glycyl sarcosine methyl ester hydrochloride salt, glycylglycine t-butyl ester hydrochloride salt, glycylglycine n-propyl ester hydrochloride salt, and glycylglycine benzyl ester hydrochloride salt. Among these glycyl sarcosine, and glycylglycine ethyl ester hydrochloride are preferable.

Some specific examples of the glycine derivatives and the salts thereof represented by the general formula (8) include, for example, 2-methylalanine, 2-ethylalanine, 2-n-propylalanine, 2,2-diethylglycine, 1-aminocyclopentanecarbonic acid, 1-aminocyclohexanecarbonic acid, 1-aminocycloheptanecarbonic acid, and the salts thereof. Among these 1-aminocyclohexanecarbonic acid is preferable.

The aminosulfuric acid derivatives and the salts thereof represented by the general formulae (9) or (10) in accordance with the invention 2 will be described herein below. The invention 2 uses at least one or two or more compounds selected from a group consisting of the aminosulfuric acid derivatives and the salts thereof as represented by the following general formulae (9) or (10).

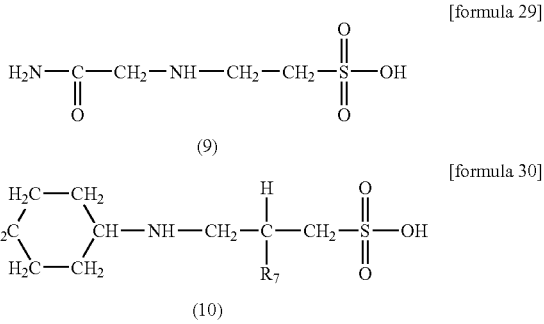

$R_7$ in the general formula (10) is a hydrogen atom or a hydroxy group.

The aminosulfuric acid derivatives represented by said general formula (9) have a chemical name such as N-(2-acetamide)-2-aminoethanesulfonic acid, N-carbamoyl-methyl taurine, or 2-[(2-amino-2-oxyethyl)amino]ethane-sulfonic acid, and are used under the name ACES. These are described as one of the constituent of Good buffer (E. Good, in Biochemistry, 5(2), pp. 467, 1966) for biological use. However, the use as parakeratosis inhibitor agent, pore-shrinking agent, skin roughness protecting/ameliorating agent and skin preparation for external use is not known yet.

The aminosulfuric acid derivatives as represented by said general formula (10) is, if $R_7$ is a hydrogen atom, a compound which is referred to as the chemical name of 3-(cyclohexylamino)propane sulfonic acid and the like, and used under the name of CAPS. This is described as one of the constituent of Good buffer (E. Good, in Biochemistry, 5(2), pp. 467, 1966) for biological use. However, the use as parakeratosis inhibitor agent, pore-shrinking agent, skin roughness protecting/ameliorating agent and skin preparation for external use is not known yet.

The aminosulfuric acid derivatives as represented by said general formula (10) is, if $R_7$ is a hydroxyl group, a compound which is referred to by the chemical name of 3-(cyclohexylamino)-2-hydroxy-propane-sulfonic acid and the like, and is used under the name of CAPSO. This is described in the U.S. Pat. No. 4,169,950 and U.S. Pat. No. 4,246,194, as one of buffers for biological use. However, the use as parakeratosis inhibitor agent, pore-shrinking agent, skin roughness protecting/ameliorating agent and skin preparation for external use is not known yet.

The salts used for formation of salts of said aminosulfuric acid derivatives in accordance with the invention 2 includes, but not limited to, for example, some inorganic salts such as hydrochloride salts, sulfate salts, phosphate salts, hydrobromide salts, sodium salts, potassium salts, magnesium salts, calcium salts, and ammonium salts, and some organic salts, such as acetate salts, lactate salts, maleate salts, fumarate salts, tartrate salts, citrate salts, methane sulfonic acid salts, p-toluene sulfonic acid salts, triethanolamine salts, diethanolamine salts, and amino acid salts. Said salt compounds of the aminosulfuric acid used in the invention 2 can be prepared in accordance with well known preparation method.

The glycine derivatives and the salts thereof as represented by said general formulae (6), (7), or (8) in accordance with the invention 2 as well as the aminosulfuric acid derivatives and the salts thereof as represented by said general formulae (9) or (10) are for example commercially marketed and readily available as reagents. These can be synthesized in accordance with well-known preparation methods as well.

The glycine derivatives and the salts thereof as represented by said general formulae (6), (7), or (8) in accordance with the invention 2 as well as the aminosulfuric acid derivatives and the salts thereof as represented by said general formulae (9) or (10) have excellent capabilities of inhibiting parakeratosis, and of reducing the pores, as will be proven later in this document. At least one or two or more compounds selected from a group consisting of glycine derivatives and the salts thereof as represented by said general formulae (6), (7), or (8) in accordance with the invention 2 as well as the aminosulfuric acid derivatives and the salts thereof as represented by said general formulae (9) or (10) are useful for the parakeratosis inhibitor agent and the pore-shrinking agent, as well as the skin roughness preventing/ameliorating composition.

The parakeratosis inhibitor agent, pore-shrinking agent, and skin roughness protecting/ameliorating agent containing as effective ingredient at least one or two or more compounds selected from a group consisting of glycine derivatives and the salts thereof as represented by said general formulae (6), (7), or (8) as well as the aminosulfuric acid derivatives and the salts thereof as represented by said general formulae (9) or (10) are also useful. The parakeratosis inhibitor agent, pore-shrinking agent, and skin roughness protecting/ameliorating agent may be preferably applied in the form of skin preparation for external use to, for example, ameliorate the conspicuous pores of the nose and cheeks and ameliorate the skin roughness as facial use, and ameliorate the conspicuous pores after leg epilation and ameliorate the skin roughness as body use.

The parakeratosis inhibitor agent, pore-shrinking agent, and skin roughness protecting/ameliorating agent in accordance with said invention 2 is a novel and useful application based on the discovery of said novel capabilities of said glycine derivatives and aminosulfuric acid derivatives in accordance with said invention 2.

Said parakeratosis inhibitor agent, the pore-shrinking agent and the skin roughness protecting/ameliorating agent in accordance with the invention 2 has a wide usage range of application, and may be applied in a variety of fields. Said fields include, for example, cosmetics including medicated cosmetics, medicines, and foods, and these are preferable.

At least one or two or more compounds selected from a group consisting of the glycine derivatives and the salts thereof as represented by the general formulae (6), (7), or (8) and the aminosulfuric acid derivatives as represented by the general formulae (9) or (10) in accordance with the invention 2 may be blended with a skin preparation for external use to prepare as a skin preparation for external use having capabilities of parakeratosis inhibition, pore reduction, and skin roughness prevention/amelioration.

The skin preparation for external use containing at least one or two or more compounds selected from a group consisting of the glycine derivatives and the salts thereof as represented by the general formulae (6), (7), or (8) and the aminosulfuric acid derivatives as represented by the general formulae (9) or (10) in accordance with the invention 2 will be therefore useful as the skin preparation for external use, which exhibits the effect of parakeratosis inhibition, pore reduction, and skin roughness prevention/amelioration.

The skin preparation for external use in accordance with the invention 2 can be suitably used as a pore-shrinking agent, a facial cosmetics for ameliorating the conspicuous pores of the nose and cheeks, a facial cosmetics for particularly preventing and ameliorating the skin roughness, a skin preparation for external use for ameliorating the conspicuous pores of legs after epilation.

When said glycine derivatives and the salts thereof and said aminosulfuric acid derivatives and the salts thereof in accordance with the invention 2 are included in the composition such as parakeratosis inhibitor agent, pore-shrinking agent, and skin roughness protecting/ameliorating agent, the effective amount for exhibiting the capabilities should be contained, more specifically the contained amount is preferably 0.001 to 20.0 weight % of said composition, more preferably 0.01 to 10.0 weight %, and most preferably 0.2 to 5.0 weight %. If said glycine derivatives and the salts thereof and said aminosulfuric acid derivatives and the salts thereof are used as a mixture, the upper limit of the total contained amount is preferably equal to or less than 20.0 weight %, more preferably equal to or less than 10.0 weight %, and most preferably equal to or less than 5.0 weight %.

The composition such as the parakeratosis inhibitor agent, pore-shrinking agent, functional skin preparation for external use in accordance with the invention 1 and the composition such as the parakeratosis inhibitor agent, pore-shrinking agent, skin roughness protecting/ameliorating agent, and skin preparation for external use in accordance with the invention 2 may also contain appropriately the ingredient used in the ordinary skin preparation for external use including cosmetics and medicines, such as oils, surfactants, powders, coloring agents, water, alcohols, viscosity improvers, chelating agents, silicone, antioxidants (oxidation inhibitors), UV absorbers, moisturizers, fragrances, any medical properties, artificial preservatives, neutralizing agents, pH regulators and the like.

Among these arbitrarily blended ingredients, some specific examples of oils include for example: liquid oils such as avocado pear oil, Camellia oil, turtle bean oil, Macadamia nuts oil, corn oil, mink oil, olive oil, Canoga oil, egg yolk oil, sesame seed oil, Persic oil, wheat germ oil, Camellia sasanqua oil, caster oil, linseed oil, safflower oil, cotton oil, evening primrose oil, eno oil, soybean oil, peanut oil, tea seed oil, kaya oil, rice bran oil, Chinese tung tree wood oil, Japanese tung tree wood oil, jojoba oil, germ oil, triglycerine, trioctanic acid glyceride, and tri-isopalmitin acid glycerine; solid oil/fat such as cocoa butter, coconut butter, horse fat, hardened coconut oil, palmoil, beef tallow, mutton tallow, hardened beef tallow, palm kernel oil, lard, Japan tallow kernel oil, hardened oil, Japan tallow, and hardened castor oil; hydro carbons such as beeswax, candelilla wax, carnauba wax, lanolin, lanolin acetate, liquid lanolin, sugar cane wax, fatty acid isopropyl lanolin, hexyl laurate, reduced lanolin, jojoba wax, hard lanolin, polyoxyethylene (POE hereinafter), lanolin alcohol ether, POE lanolin alcohol acetate, lanolin fatty acid polyethylene glycol, and POE hydrogenated lanolin alcohol ether, carbohydrates such as liquid paraffin, ozokerite, squalane, paraffin, ceresin, squalane, Vaseline, and microcrystalline wax; higher fatty acids such as isopropyl myristate, cetyl octoate, octyldodecil myristate, isopropyl palmitate, butyl stearate, hexyl laurate, myristyl myristate, decyl oleate, hexyldecyl dimethyl-octoate, cetyl lactate, myristyl lactate, lanolin acetate, isocetyl stearate, isocetyl iso-stearate, 12-hydroxy cholesteryl stearate, di-2-ethylhexylic acid ethyleneglycol, dipentaerythritol fatty acid ester, N-alkylglycol monoisostearate, neopentylglycol dicaprate, diisostearyl malate, glycerine di-2-heptyl undecatoic acid, tri-methylol propane tri-2-ethylhexyl acid, tri-methylol propane triisostearate, pentaerythritol tetra-2-ethylhexyl acid, glycerine tri-2-ethylhexyl acid, tri-methylol propane triisostearate, cetyl-2-ethylexanoate, 2-ethylhexyl-palmitate, glycerine trimyristate, glyceride tri-2-heptyl undecatoic acid, methyl ester of castor oil fatty acid, oleate oil, acetoglyceride, palmitate-2-heptyl undecyl, diisopropyl adipate, N-lauroyl-L-glutamic acid-2-octyldodecil ester, di-2-heptylundecyl adipate, di-2-ethylhexyl sebacic acid, myristate-2-hexyldecyl, palmitate-2-hexyldecyl, adipate-2-hexyldecyl, diisopropyl sebacate, and succinate-2-ethylhexyl, higher fatty acids such as lauric acid, myristic acid, palmitic acid, stearic acid, behenic acid, oleic acid, 12-hydroxy-stearic acid, undecylenic acid, lanolin fatty acid, isostearic acid, linolic acid, linolenic acid, and eicosapentaenoic acid; higher alcohols of straight/branched chain such as lauryl alcohol, cetyl alcohol, stearyl alcohol, behenyl alcohol, myristyl alcohol, oleyl alcohol, cetostearyl alcohol, monostearyl glycerine ether (butyl alcohol), 2-decyltetradecinol, lanolin alcohol, cholesterol, phytosterol, hexyldodecanol, isostearyl alcohol, octyldodecanol; silicone oil such as dimethylpolysiloxane, and methylphenylpolysiloxane perfluorocarbons; and perfluoropolyethers such as perfluorohexane, and triperfluoro-n-butylamine.

The surfactants include, for example, fatty acid soaps such as raw material of soap, sodium laurate, and sodium palmitate; higher alkylsulfate ester salts such as sodium laurylsulfate, and potassium laurylsulfate; alkyl-ether sulfate ester salts such as POE triethanolamine laurylsulfate, and POE sodium laurylsulfate; N-acylsarcosinate such as sodium lauroyl sarcosine; higher fatty acid amidsulfonic acid such as sodium N-myristyl-N-methyl taurine, and palm oil fatty acid sodium methyltauride; phosphate ester salts such as POE stearyl ether phosphate; sulfosuccinic acid salts such as sodium monolauroyl-monoethanolamide POE sulfosuccinate, and sodium lauryl polypropylene glycol sulfosuccinate; alkylbenzene sulfonic acids such as sodium linear dodecyl benzene sulfonic acid, triethanolamine linear dodecyl benzene sulfonic acid;

N-acyl-glutamic acid salts such as disodium N-stearoyl glutamic acid, and monosodium N-stearoyl glutamic acid; higher fatty acid ester sulfate ester salts such as sodium hardened palm oil fatty acid glycerine sulfate; sulfated oil such as turkey red oil; anionic surfactants such as POE alkyl-ether carbonate, POE alkylaryether carbonate salts, higher fatty acid ester sulfonate salts, ester secondary alcohol sulfate salts, ester higher fatty acid alkyloylamidsulfate salts, sodium lauroyl monoethanolamide succinate, and sodium casein; alkyl trimethyl ammonium salts such as stearyl trimethyl ammonium chloride, lauryl trimethyl ammonium chloride; dialkyl dimethyl ammonium salts such as distearyl dimethyl ammonium chloride; alkyl-pyridinium salts such as cetyl pyridinium chloride; cationic surfactants such as alkyl quaternary ammonium salts, alkyldimethylbenzyl ammonium salts, alkylisoquinolinium salts, dialkylmoriphonium salts, POE alkylamine, alkylamine salts, polyamine fatty acid derivatives, amyl alcohol fatty acid derivatives, and benzalkonium chloride;

dipolar surfactants including imidazoline-type bipolar surfactants such as disodium 2-cocoyl-2-imidazolinium hydroxide-1-carboxyethyloxy salts, and betaine-type dipolar surfactants such as amidebetaine, and sulfobetaine;

sorbitan fatty acid esters such as sorbitan monooleate, sorbitan monoisostearate, sorbitan monolaurate, sorbitan monopalmitate, and sorbitan trioleate, glycerine polyglycerine fatty acids such as glycerine monocottonseed oil fatty acid, glycerine monostearate, glycerine sesquioleate, and monostearate glycerine malate salts, propylene glycol fatty acid esters such as propylene glycol monostearate, lipophilic nonionic surfactants such as hardened caster oil derivatives, glycerine alkylether, and POE-methyl polysiloxane copolymers;

esters POE sorbitan fatty acids such as POE sorbitan monooleate, and POE sorbitan monostearate, esters POE sorbit fatty acid such as POE sorbit monolaurate, POE sorbit monooleate, and POE sorbit monostearate, POE glycerine fatty acid esters such as POE glycerine monooleate, and POE glycerine distearate, POE fatty acid esters such as POE monooleate, POE distearate, and POE monodioleate, POE alkylethers such as POE laurylether, POE oleylether, POE cholestanol ester, POE alkylphenylethers such as POE octylphenylether, and POE nonylphenylether, POE POP alkylethers such as POE POP monobutyl ether, POE POP cetylether, and POE POP glycerine ether, POE castor oil hardened castor oil derivatives such as POE caster oil, POE hardened castor oil, POE hardened castor oil monoisostearate, and POE hardened castor oil maleate, POE beeswax lanolin derivatives such as POE sorbit beeswax, alkanolamides such as palm oil fatty acid diethanolamide, and fatty acid isopropanolamide, hydrophilic nonionic surfactants such as POE propylene glycol fatty acid esters, POE fatty acid amide, POE alkylamine, saccharose fatty acid ester, and alkyletoxydimethylamine oxide.

Powders include, for example, mica, talc, kaolin, sericite, muscovite, phlogopite, synthetic mica, lepidolite, black mica, lithia mica, synthetic mica, calcium carbonate, magnesium carbonate, silicic acid anhydride (silica), aluminium silicate, barium silicate, calcium silicate, magnesium silicate, strontium silicate, aluminium oxide, barium sulfate, iron oxide red, yellow iron oxide, black iron oxide, cobalt oxide, ultramarine, Prussian blue, titan oxide, zinc oxide, titan mica (titanium oxide coated mica), argentine, bismuth oxychloride, boron nitride, red 228, red 226, blue 404, polyethylene powder, methyl polymethacrylic acid powder, polyamide resin powder (nylon powder) cellulose powder, organopolysiloxane elastomer, aluminum powder, and copper powder.

Alcohols includes, for example, lower alcohols such as methanol, ethanol, propanol, and isopropanol; cholesterol, sitosterol, and lanosterol.

Thickeners include, for example, water-soluble macromolecular substances including vegetable macromolecular substances such as Arabic rubber, tragacanth gum, galactan, callop gum, Cyamoposis gum, carrageenan, pectin, agar, and starch (corn, wheat, potato, rice), macromolecular substances of microorganism such as dextran, and pullulant, macromolecular starches such as carboxymethyl starch, and methylhydroxypropyl starch, animal macromolecular substances such as collagen, casein, and gelatin, macromolecular substances of celluloses such as methyl cellulose, nitro cellulose, ethyl cellulose, hydroxy ethyl cellulose, sodium cellulose sulfate, hydroxy propyl cellulose, carboxy methyl cellulose, and crystal cellulose, macromolecular substances of alginate such as sodium alginate, and propylene glycol ester alginate, macromolecular substances of vinyl such as polyvinyl methyl ether, and carboxy vinyl polymer, POE macromolecules, macromolecules of POE polyoxy propylene copolymer, acrylic macromolecular substances such as sodium polyacrylate, and amide polyacrylate, water-soluble inorganic macromolecules such as polyethylene imine, cation polymer, bentonite, aluminium magnesium silicate, raponite, hectolyte, and silicate unhydride.

Chelating agents include, for example, citramalic acid, agaric acid, glyceric acid, shikimic acid, hinokitiol, gallic acid, tannic acid, caffeic acid, ethylenediamine tetraacetate, ethyleneglycol diamine tetraacetate, diethylene triamine pentacetate, phytic acid, polyphosphoric acid, metaphosphate, and analogues of these agents, as well as alkaline metallines thereof, and ester carbonate.

UV absorbers include, for example, UV absorbers of benzoic acids such as paraaminio benzoic acid; UV absorbers of anthranilic acid such as methyl anthranilate; UV absorbers of salicylic acids such as octyl salicylate, UV absorbers of cinnamic acids such as isopropyl paramethoxy cinnamic acid, and octyl paramethoxy cinnamic acid; other UV absorbers such as urocanic acid, and ethyl urocanic acid.

Moisturizing agents include, for example, polyethylene glycol (PEG, hereinafter), propylene glycol, dipropylene glycol, 1,3-butylene glycol, glycerin, deglycerin, xylitol, maltitol, maltose, D-mannitol, glucose, fructose, sodium chondroitin sulfuric acid, sodium hyaluronic acid, sodium lactate, glucosamine, and cyclodextrin.

Medicated ingredients include, for example, vitamins such as vitamin A oil, retinol, retinol palmitate, pyridoxine hydrochloride, benzyl nicotinic acid, nicotinamide, dl-alpha-tocopherol nicotinate, magnesium ascorbate phosphate, vitamin $D_2$, dl-alpha-tocopherol, pantothenic acid, and biotin; anti-inflammatory agents such as azulene, glycyrrhizin, whitening agents such as arbutin; hormones such as estradiol; astringency agents such as zinc oxide, and tannic acid; tonic agents such as L-menthol, and camphor; and other agents such as lysozyme chloride, pyridoxine hydrochloride, and sulfur. A variety of extracts that exhibits various medical effects can also be blended. More specifically, the extracts include, for example, Saururae extract, cork tree bark extract, Glycyrrhiza extract, peony extract, mountain bark extract, loofah extract, Saxifraga extract, eucalyptus extract, clove extract, marronnier extract, knapweed extract, seaweed extract, and thyme extract.

Preservative agents include, for example, benzoic acid, salicylic acid, ester paraoxysalicylic acid (methyl paraben, ethyl paraben, butyl paraben, etc.) sorbic acid, parachlormetacresol, hexachlorophene, benzalkonium chloride, chlorhexidine chloride, trichlorocarbanilide, photosensitive agent, and phenoxyethanol.

Some other agents can be blended to the composition in accordance with the present invention, including neutralizing agents such as 2-amino-2-methyl-1-propanol, 2-amino-2-methyl-1,3-propandiol, potassium hydroxide, potassium hydroxide, triethanolamine, sodium carboxide; pH regulators such as lactic acid, citric acid, glycol acid, succinic acid, dihydroxysuccinic acid, malic acid, sodium bicarbonate, and ammonium bicarbonate; anti-oxidants such as ascorbic acid, alpha-tocopherol, and carotenoid.

It should be appreciated that the above ingredients are merely examples, and the invention is to be considered not to be limited thereto. These ingredients can be blended in any appropriate combination, in accordance with the recipe convenable to the form desired.

The composition including the parakeratosis inhibitor agent, pore-shrinking agent, and functional skin preparation for external use in accordance with the invention 1 as well as the composition including the parakeratosis inhibitor agent, pore-shrinking agent, skin roughness protecting/ameliorating agent, and skin preparation for external use in accordance with the invention 2 may be prepared through the conventional procedure after blending some of said ingredients.

The composition including the parakeratosis inhibitor agent, pore-shrinking agent, and functional skin preparation for external use in accordance with the invention 1 as well as the composition including the parakeratosis inhibitor agent, pore-shrinking agent, skin roughness protecting/ameliorating agent, and skin preparation for external use in accordance with the invention 2 can be applied to such forms as medicinal drugs, quasi-drugs (ointments, toothpaste, etc.) and cosmetics (facial wash, skin milk, cream, gel, essence (serum), basic skin care including packs and masks; makeup cosmetics including foundation, lip stick; oral cosmetics, fragrant cosmetics, hair cosmetics, body cosmetics). It should be appreciated here that the applicable form of composition including the parakeratosis inhibitor agent, pore-shrinking agent, and functional skin preparation for external use in accordance with the invention 1 as well as the composition including the parakeratosis inhibitor agent, pore-shrinking agent, skin roughness protecting/ameliorating agent, and skin preparation for external use in accordance with the invention 2 are not to be limited thereto.

The formulation may come in many forms, including water-soluble, soluble, emulsified, oil-based, gel, ointment, aerosol, 2 layers of water-oil, 3 layers of water-oil-powder, and the like.

The present invention provides a vernal fresh skin by using the composition including the parakeratosis inhibitor agent, pore-shrinking agent, and functional skin preparation for external use in accordance with the invention 1 as well as the composition including the parakeratosis inhibitor agent, pore-shrinking agent, skin roughness protecting/ameliorating agent, and skin preparation for external use in accordance with the invention 2, such that skin condition can be kept better by inhibiting the parakeratosis, or improving, and shrinking the pores to prevent the conspicuous pores.

EMBODIMENTS

The present invention will be described in greater details with reference to some preferred embodiments herein below. The blending quantity is weight % unless otherwise notified.
1. Regarding the Invention 1

First Embodiment

Parakeratosis Inhibition Effect Test

A 3 weight % water solution (including 30 weight % ethanol) was prepared as the evaluation specimen of the glycine derivatives in accordance with the invention 1. The pH was regulated to the range between 7.0 to 7.5, by using hydrochloric acid and sodium hydroxide. When the solubility was low, the solution was adjusted accordingly.

100 microliters of 10 weight % oleic acid (solvent: ethanol) was applied to the back of hairless mice (HR-1, Hoshino laboratory animals). Thereafter, 100 microliters of sample solution was applied (glycine derivatives in accordance with said invention 1) at each time. This procedure was repeated for 3 days. The day after the application, the skin condition of the backs was observed by using a CCD camera to evaluate the skin roughness (stratified ablation of the skin surface stratum corneum and red spots). The skin condition was evaluated visually, with scoring the skin condition of control application to 2.0 and the skin condition of no roughness to 0.0, in a 0.25 point step in response to the skin condition. At the same time, the skin surface stratum corneum of the back of hairless mice was peeled off by using a tape for staining the nucleus with haematoxylin to observe the degrees of parakeratosis (parakeratosis level) and evaluate in 0.25 step in the range from 1.0 to 3.0. The higher evaluation points indicates the larger number of parakeratotic corneocytes count, i.e., severer parakeratosis. The result is shown in Table 1 below.

TABLE 1

| Sample | Concentration (weight %) | Visual (mean of 4 mice) | Evaluation Parakeratosis (mean of 4 mice) |
| --- | --- | --- | --- |
| control solution | — | 2.0 | 2.0 |
| sarcosine | 3 | 1.3 | 1.2 |
| glycylglycine | 3 | 1.2 | 1.2 |
| glycyl-glycylglycine (reference) | 1 | 1.9 | 2.0 |
| glycine amide(reference) | 3 | 1.9 | 2.1 |
| glycine benzyl ester HCL | 3 | 1.3 | 1.2 |
| glycine ethyl ester HCL | 3 | 1.2 | 1.1 |
| glycine n-butyl ester HCL | 3 | 1.6 | 1.5 |
| glycine t-butyl ester HCL | 3 | 1.6 | 1.5 |
| glycine n-propyl ester HCL | 3 | 1.4 | 1.4 |
| phenaceturic acid | 3 | 1.2 | 1.1 |
| N-acetyl-L-glutamic acid | 3 | 1.2 | 1.2 |
| N-benzoyl-L-glutamic acid | 3 | 1.7 | 1.6 |
| N-benzenesulfonyl-L-glutamic acid | 3 | 1.6 | 1.6 |
| N-acetyl-L-aspartic acid | 3 | 1.4 | 1.5 |
| beta-alanine | 3 | 1.6 | 1.5 |
| beta-alanine ethyl ester HCL | 3 | 1.0 | 1.2 |
| isonipecotinic acid | 3 | 1.6 | 1.5 |
| guanidinoisonipecotinic acid (reference) | 3 | 2.0 | 2.2 | concentration: concentration in aqueous solution including 30 weight % ethanol.

As can be clear from Table 1, it was shown that sarcosine, glycylglycine, glycine benzyl ester hydrochloride, glycine ethyl ester hydrochloride, glycine n-butyl ester hydrochloride, glycine t-butyl ester hydrochloride, glycine n-propyl ester hydrochloride, phenaceturic acid, N-acetyl-L-glutamic acid, N-benzoyl-L-glutamic acid, benzenesulfonyl-L-glutamic acid, N-acetyl-L-aspartic acid, beta-alanine, beta-alanine ethyl ester hydrochloride, isonicopetinic acid have the effect of inhibiting parakeratosis.

Second Embodiment

Effect of Shrinking Human Pores

An experiment of application of sample twice a day for a month on the cheek of healthy male subjects, was conducted with each group consisting of 5 individuals. 3 weight % solution of the glycine derivatives in accordance with the invention 1 (including 15 weight % of ethanol) was prepared. pH was regulated to the range between 7.0 and 7.5, by using hydrochloric acid and/or sodium hydroxide. Control was 15 weight % ethanol solution. Said 3 weight % solution was applied to one side and said control solution was applied to the other side.

Replicas were prepared prior to and after the application to observe the change of form of pores in the same spot under a three-dimensional laser scanning microscope. The size of pores was evaluated visually 13 steps from 1 to 13 (larger number indicates larger pore size), and the difference between the resulted evaluations before/after the application experiment was then calculated to study the effectiveness of each specimen. The result is shown in Table 2 below.

TABLE 2

| Sample | Replica Evaluation (mean of n = 5) |
|---|---|
| control solution | 0.2 |
| sarcosine | −1.3 |
| glycylglycine | −1.0 |
| N-acetyl-L-glutamic acid | −0.8 |
| beta-alanine | −0.9 |
| phenaceturic acid | −0.8 |

As can be appreciated from Table 2, pore-shrinking effect was observed in sarcosine, glycylglycine, N-acetyl-L-glutamic acid, beta-alanine, and phenaceturic acid.

Third Embodiment

Effect of Shrinking Human Pores by Glycylglycine

Since we obtained a good result from glycylglycine in the embodiment 2, we conducted an application experiment of glycylglycine three times a day (0.1 milliliter each) on the cheek of 21 healthy adult males (age of 20s to 50s, average 40.4 years old) for a period of one month. 1.6% (w/w) glycylglycine solution (pH regulated to 7.0) including 15% (w/w) ethanol, and 15% (w/w) ethanol solution (control) was prepared, for applying the same to each one side cheek.

By obtaining a cheek replica (Silflo) before and after the continuous application, the surface area of conical portion was measured by a three-dimensional analysis system (Okuri et al., Japan Society of Dermatology Annual Meeting Program/Abstract, 2004, 104, pp. 601) by means of wide view confocal microscope HD100D (lasertech).

For the surface area recognized as pore portion within the replica measuring area of 3.34 mm by 3.34 mm, the conical portion surface area (mm2) and the ratio thereof before and after the application is shown in Table 3. From Table 3, The ratio among the panel that the surface area of glycylglycine applied side was decreased more than 10% when compared to the control application side (glycylglycine side was shrunk), the panel that the variation was within 10% and no noticeable change observed (no change), and the panel that the control application side was decreased more than 10% (other side was shrunk) was 13:5:3.

When averaging the surface area ratio before and after the application, the side of control solvent solution was 102%, while the side of glycylglycine was reduced to 89%. By evaluating this surface area ratio with t-analysis, we obtained p=0.019, indicating significant shrinkage of pore area in the glycylglycine applied side (see FIG. 1). FIG. 1 shows the surface area value after application as mean±S.D. based on the surface area before application as the value of 100.

In the photographic evaluation, it was shown that the conspicuous pores in the glycylglycine applied side were ameliorated in comparison to the pores in the ethanol applied side.

TABLE 3

| | control | | | glycylglycine | | |
|---|---|---|---|---|---|---|
| Panel # | before (mm$^2$) | after (mm$^2$) | after/ before | before (mm$^2$) | after (mm$^2$) | after/ before |
| 1 | 0.3342 | 0.3475 | 1.040 | 1.2116 | 1.0541 | 0.8700 |
| 2 | 0.8421 | 0.8669 | 1.029 | 0.4486 | 0.5801 | 1.2931 |
| 3 | 0.6219 | 0.4283 | 0.689 | 0.8839 | 0.6728 | 0.7612 |
| 4 | 1.1352 | 1.2889 | 1.135 | 1.3700 | 1.3879 | 1.0131 |
| 5 | 1.3080 | 1.4473 | 1.106 | 1.3475 | 1.2057 | 0.8948 |
| 6 | 0.6229 | 0.8769 | 1.408 | 1.3982 | 1.3727 | 0.9818 |
| 7 | 1.1416 | 1.1774 | 1.031 | 1.4428 | 1.5166 | 1.0512 |
| 8 | 1.0761 | 1.1376 | 1.057 | 1.3576 | 1.4427 | 1.0627 |
| 9 | 0.7169 | 0.8149 | 1.137 | 1.1740 | 1.2368 | 1.0535 |
| 10 | 1.2381 | 1.2924 | 1.044 | 0.8110 | 0.6078 | 0.7494 |
| 11 | 0.4878 | 0.4334 | 0.888 | 0.6962 | 0.3675 | 0.5279 |
| 12 | 0.7902 | 0.6726 | 0.851 | 0.6590 | 0.4880 | 0.7405 |
| 13 | 0.7794 | 0.7434 | 0.954 | 1.4280 | 1.1250 | 0.7878 |
| 14 | 1.2425 | 1.1065 | 0.891 | 0.9402 | 0.5977 | 0.6357 |
| 15 | 0.7336 | 0.9256 | 1.262 | 1.5987 | 1.3739 | 0.8594 |
| 16 | 0.7259 | 0.6823 | 0.940 | 0.6546 | 0.2691 | 0.4111 |
| 17 | 0.9092 | 0.9757 | 1.073 | 0.8863 | 1.2348 | 1.3932 |
| 18 | 1.1332 | 0.9591 | 0.846 | 1.3482 | 1.2053 | 0.8940 |
| 19 | 1.2571 | 1.2787 | 1.017 | 0.8182 | 1.0498 | 1.2831 |
| 20 | 0.6886 | 0.5872 | 0.853 | 0.6559 | 0.3669 | 0.5594 |
| 21 | 0.6764 | 0.7510 | 1.110 | 0.8830 | 0.6778 | 0.7676 |
| mean | — | — | 1.017 | — | — | 0.8853 |
| S.D. | — | — | 0.158 | — | — | 0.2597 |

2. About the Invention 2

Fourth Embodiment

Parakeratosis Inhibition Effect Test

The samples to be evaluated of the glycine derivatives and the salts thereof as well as the aminosulfuric acid derivatives and the salts thereof in accordance with the invention 2 were prepared mainly 3 weight % solution (including 30 weight % ethanol, excluding Hydantoic acid and ACES which include 20 weight % ethanol). pH was regulated by using hydrochloric acid or sodium hydroxide to be 7.0 to 7.5. When the solubility was low, then the solution was prepared accordingly.

100 microliters of 10 weight % oleic acid (solvent: ethanol) was applied to the back of Hairless mice (HR-1, Hoshino laboratory animals) Thereafter, 100 microliters of sample solution (glycine derivatives in accordance with the invention 2) was applied thereon at each time. This procedure was repeated for 3 days. The day after the application, the skin condition of the backs was observed by using a CCD camera to evaluate the skin roughness (stratified ablation of the skin surface stratum corneum and red spots). The skin condition was evaluated visually, with scoring the skin condition of control application to 2.0 and the skin condition of no roughness to 0.0, in a 0.25 point step in response to the skin condition. At the same time, the skin surface stratum corneum of the back of hairless mice was peeled off by using a tape for staining the nucleus with haematoxylin to observe the degrees of parakeratosis and evaluate in 0.25 step in the range from 1.0 to 3.0. The higher evaluation points indicates the larger number of parakeratotic corneocytes count, i.e., severer parakeratosis. The result is shown in Table 4 below.

TABLE 4

| Sample | Concentration (weight %) | Visual (mean of 4 mice) | Evaluation Parakeratosis (mean of 4 mice) |
|---|---|---|---|
| control solution | — | 2.0 | 2.0 |
| hydantoic acid | 3 | 1.4 | 1.3 |
| N-ethylglycine | 3 | 1.3 | 1.2 |
| N-phenylglycine | 3 | 1.3 | 1.2 |
| glycylglycine ethyl ester HCL | 3 | 1.3 | 1.1 |
| glycyl-sarcosine | 3 | 1.5 | 1.4 |
| glycine-amide HCL (reference) | 3 | 1.9 | 2.0 |
| hippuric acid (reference) | 1 | 1.8 | 1.9 |
| betaine (reference) | 3 | 1.8 | 1.8 |
| bicine (reference) | 3 | 1.9 | 2.0 |
| nitrilotriacetate (reference) | 0.4 | 1.9 | 2.0 |
| N,N-dimethylglycine (reference) | 3 | 2.1 | 2.3 |
| tricine (reference) | 2 | 2.0 | 2.1 |
| N-acetylglycine (reference) | 3 | 1.9 | 2.0 |
| ethyl-1-piperidine acetate (reference) | 3 | 1.8 | 1.9 |
| methylmorpholino acetate (reference) | 3 | 1.9 | 2.0 |
| hydantoin (reference) | 1 | 2.1 | 2.0 |
| phosphomethylglycine (reference) | 1 | 1.9 | 2.1 |
| ACES | 1 | 1.4 | 1.2 |
| CAPS | 3 | 1.3 | 1.2 |
| CAPSO | 3 | 1.3 | 1.1 |
| CHES (reference) | 3 | 1.8 | 1.9 |
| CABS (reference) | 3 | 1.9 | 2.0 |
| MOPS (reference) | 3 | 1.9 | 2.1 |
| TAPS (reference) | 3 | 2.0 | 2.1 | concentration: concentration in aqueous solution including 30 weight % ethanol (excluding hydantoic acid and ACES which are concentration of aqueous solution including 20 weight % ethanol).

As can be clear from Table 4, it was shown that hydantoic acid, N-ethylglycine, N-phenylglycine, glycylglycine ethyl ester hydrochloride, glycyl sarcosine, ACES, CAPS, CAPSO have the effect of inhibiting parakeratosis. On the other hand, as can be seen from the result of reference materials, for example, carboxyl group replaced with amide (i.e., glycine-amide hydrochloride and hydantoin) did not exhibit such effect. The modification of amino group did exhibit effect in case of N-ethyl and N-phenyl groups, however the effect disappeared in case of N,N-dimethyl and N-acetyl groups. The effect was not recognized for CHES (2-(N-cyclohexy-lamino)ethane sulfonic acid), CABS (4-(cyclohexylamino)-1-butane sulfonic acid), MOPS (3-(N-morpholino)propane sulfonic acid), TAPS (N-tris(hydroxymethyl)methyl-3-aminopropane sulfonic acid), all of which are component compounds of the Good buffer solution and are aminosulfuric acid derivatives.

Fifth Embodiment

Effect of Shrinking Human Pores

An experiment of application of sample twice a day for a month on the cheek of healthy male subjects, was conducted with each group consisting of 5 individuals. 3 weight % solution of the glycine derivatives and the salts thereof as well as the aminosulfuric acid derivatives and the salts thereof in accordance with the invention 2 (including 15 weight % of ethanol), 2 weight % solution of ACES (including 15 weight % of ethanol), 3 weight % solution of CAPS (including 15 weight % of ethanol), and 3 weight % solution of CAPSO (including 15 weight % of ethanol) were prepared. pH was regulated to the range between 7.0 and 7.5, by using hydrochloric acid and/or sodium hydroxide. 15 weight % ethanol solution was used as control. Said sample solutions was applied to one side, and said control solution was applied to the other side.

Replicas were prepared prior to and after the application to observe the change of form of pores in the same spot under a three-dimensional laser scanning microscope. The size of pores was evaluated visually 13 steps from 1 to 13 (larger number indicates larger pore size), and the difference between the resulted evaluations before/after the application experiment was then calculated to study the effectiveness of each specimen. The result is shown in Table 5 below.

TABLE 5

| Sample | Concentration (weight %) | Replica Evaluation (mean of n = 5) |
|---|---|---|
| control solution | — | 0.3 |
| N-ethylglycine | 3.0 | −1.4 |
| N-phenylglycine | 3.0 | −1.0 |
| hydantoic acid | 3.0 | −0.8 |
| glycyl sarcosine | 3.0 | −0.8 |
| ACES | 2.0 | −1.5 |
| CAPS | 3.0 | −1.4 |
| CAPSO | 3.0 | −1.6 |

As can be seen from Table 5, N-ethylglycine, N-phenylglycine, hydantoic acid, glycyl sarcosine, ACES, CAPS, CAPSO demonstrated the effect of pore-shrinking.

Sixth Embodiment

Parakeratosis Inhibition Effect and Pore-Shrinking Effect on Human Skin by the Application of N-Ethylglycine In the pore-shrinking effect test on human skin as described in the embodiment 5, the application of N-ethylglycine was further studied about the amelioration of parakeratosis by measuring the number of nuclear cell of skin surface stratum corneum, obtained by means of a tape. Replica was used to actually measure the pore size within the area of 3.34 mm by 3.34 mm to evaluate the pore-shrinking effect.

More specifically, the skin surface stratum corneum was sampled by means of carton tape (Nichiban, Co. Ltd.) only after the application of sample, Hoechst 33342 solution dissolved in PBS to 0.1 mg/ml was then added, and after the sample was placed in a dark place for 20 minutes, the number of nuclear cells within the area of 12 mm by 34 mm by using a fluorescent microscope. For the replicas made by using silflo (Flexico, Co. Ltd.) was measured before and after the application to capture three-dimensional surface form within the same area (3.34 mm by 3.34 mm) with a confocal microscope (HD100D, Lasertech) to measure and compare the size of pores (surface area value).

The measuring result of the number of nuclear cells is shown in FIG. 2, the change of pore area in accordance with the replica analysis is shown in FIG. 3. From these results, it was shown that the side having 3 weight % N-ethylglycine applied had fewer number of nuclear cells, and that the parakeratosis was likely tend to be inhibited. The surface area of pores was a slight decrease in the control (average of 92% as compared to pre-application status); the side with N-ethylglycine applied showed a much larger decrease (average of 73% as compared to pre-application status), so that the pore-shrinking effect of this compound was confirmed.

Seventh Embodiment

Inhibitory Effect on Skin Roughness by the Application of Oleic Acid

To study the inhibitory effect on the skin roughness by the application of oleic acid by the glycine derivatives and the salts thereof as well as the aminosulfuric acid derivatives and the salts thereof in accordance with the invention 2, the total evaporation of water (TEWL value) before and after the application was measured to compare the difference therebetween with the value of control (control solution) in order to determine the effect. The preparation of samples and the application procedure were in accordance with the embodiment 4. The TEWL value was measured by means of TEWA meter TM210 (Courage+Khazaka Inc.).

100 microliters of 10 weight % oleic acid (solvent: ethanol) was applied to the back of hairless mice (HR-1, four in each group). Thereafter, 100 microliters of sample solutions (glycine derivatives and the salts thereof as well as the aminosulfuric acid derivatives and the salts thereof) in accordance with the invention 2 were applied at each time. This procedure was repeated for 3 days. The day after the application, TEWL value of the back of mice was measured and the values were averaged. The result is shown in Table 6. The larger delta-TEWL value indicates severer aggravation of skin roughness.

TABLE 6

| Sample | Concentration (weight %) | ΔTEWL |
|---|---|---|
| control | — | 12.0 |
| hydantoic acid | 3 | 8.0 |
| N-ethylglycine | 3 | 9.0 |
| N-phenylglycine | 3 | 7.9 |
| glycylglycine ethyl ester HCL | 3 | 6.7 |
| nicotinoylglycine | 0.1 | 7.4 |
| glycineamide HCL (reference) | 3 | 12.4 |
| hippuric acid (reference) | 1 | 10.5 |
| betaine (reference) | 3 | 10.6 |
| bicine (reference) | 3 | 12.0 |
| nitrilotriacetic acid (reference) | 0.4 | 11.5 |
| N,N-dimethylglycine (reference) | 3 | 15.5 |

TABLE 6-continued

| Sample | Concentration (weight %) | ΔTEWL |
|---|---|---|
| tricine (reference) | 2 | 12.2 |
| N-acetylglycine (reference) | 3 | 14.7 |
| ethyl-1-piperidine acetate (reference) | 3 | 10.7 |
| methylmorpholino acetic acid (reference) | 3 | 10.8 |
| hydantoin (reference) | 1 | 17.6 |
| phosphonomethylglycine (reference) | 1 | 11.4 |
| ACES | 1 | 6.9 |
| CAPS | 3 | 8.1 |
| CAPSO | 3 | 7.9 |
| CHES (reference) | 3 | 12.3 |
| CABS (reference) | 3 | 11.9 |
| MOPS (reference) | 3 | 13.2 |
| TAPS (reference) | 3 | 12.0 |

As can be seen from Table 6, the application of hydantoic acid, N-phenylglycine, N-ethylglycine, glycylglycine ethyl ester hydrochloride salt, nicotinoylglycine, ACES, CAPS, CAPSO resulted in a significant decrease of delta-TEWL value as compared to the control solution, thus indicating the skin roughness protecting/ameliorating effect.

Some exemplary dosage of the skin preparation for external use in accordance with the invention 1 will be described in greater details herein below. Any of these compositions did exhibit the excellent effect of parakeratosis inhibition, pore-shrinking, and the like.

Example 1

Skin Lotion

| Prescription - Blend Ratio (% by mass) | |
|---|---|
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl-alcohol ester | 0.5 |
| (6) ethanol | 10.0 |
| (7) sarcosine | 3.0 |
| (8) purified water | balance. |

(Preparation Method)

(1) and (2) was dissolved in (8) purified water at room temperature to yield aqueous phase. Other compounds were dissolved in (6) ethanol to make solvable into the aqueous phase above. Then (7) sarcosine was added. Thereafter the sample was filtered and filled in a bottle to obtain a lotion.

Example 2

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) ester sorbitan monolauric acid | 0.5 |

-continued

| Prescription - Blend Ratio (% by mass) | |
|---|---|
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) glycylglycine | 3.0 |
| (9) glycerine | 4.0 |
| (10) ion-exchanged water | balance. |

(Preparation Method)

After each phase was prepared separately, those were blended.

Example 3

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) ester sorbitan monolauric acid | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) phenaceturic acid | 1.0 |
| (9) glycerine | 4.0 |
| (10) ion-exchange water | balance. |

(Preparation Method)

Aqueous phase and alcohol phase were prepared separately, then those were blended.

Example 4

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) ester sorbitan monolauric acid | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) N-acetyl-L-glutamic acid | 5.0 |
| (9) glycerine | 4.0 |
| (10) ion-exchanged water | balance. |

(Preparation Method)

Aqueous phase and alcohol phase were prepared separately, then those were blended.

Example 5

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) ester sorbitan-monolauric acid | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) N-acetyl-L-aspartic acid | 0.01 |
| (9) isonipecotic acid | 0.01 |
| (10) glycerine | 4.0 |
| (11) ion-exchanged water | balance. |

(Preparation Method)

Aqueous phase and alcohol phase were prepared separately, then those were blended.

Example 6

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) ester sorbitan monolauric acid | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) sarcosine | 20.0 |
| (9) glycerine | 4.0 |
| (10) ion-exchanged water | balance. |

(Preparation Method)

Aqueous phase and alcohol phase were prepared separately, then those were blended.

Example 7

Skin Lotion

| Prescription - Blend Ratio (% by mass) | |
|---|---|
| (1) 1,3-butylene glycol | 6.0 |
| (2) glycerine | 4.0 |
| (3) oleyl alcohol | 0.1 |
| (4) POE (20) ester sorbitan monolauric acid | 0.5 |
| (5) POE (15) laurylether | 0.5 |

-continued

| Prescription - Blend Ratio (% by mass) | |
|---|---|
| (6) ethanol | 10.0 |
| (7) sarcosine | 1.0 |
| (8) glycylglycine | 1.0 |
| (9) N-(2-hydroxyethyl) ethylenediamine triacetate | 0.2 |
| (10) purified water | balance. |

(Preparation Method)

(1) and (2) was dissolved in (10) purified water at room temperature to yield aqueous phase. Other compounds were dissolved in (6) ethanol to be solvable into the aqueous phase above. Then (7) sarcosine and (8) glycylglycine were added thereto. Thereafter the sample was filtered and filled in a bottle to obtain a lotion.

Example 8

Cream

| Prescription - Blend Ratio (% by mass) | |
|---|---|
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) PEG1500 | 4.0 |
| (8) POE (25) cetyl alcohol ester | 3.0 |
| (9) glycerine monostearic acid | 2.0 |
| (10) sarcosine | 0.2 |
| (11) tocopherol | 0.1 |
| (12) purified water | balance |

(Preparation Method)

(6) and (7) were added to (12) purified water and then heated to 70 degrees centigrade. (1) to (5) were dissolved while heated, (8) to (9), (11) were then added and heated to 70 degrees centigrade, and thereafter (10) is added thereto. The latter was added to the former aqueous phase blend, emulsion particulates were homogenized by using a homogenizing mixer, then degassed, filtered, and cooled to yield cream.

Example 9

Cream

| Prescription - Blend Ratio (% by mass) | |
|---|---|
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) PEG1500 | 4.0 |
| (8) POE (25) cetyl alcohol ester | 3.0 |
| (9) glycerine monostearic acid | 2.0 |
| (10) glycylglycine | 10.0 |
| (11) tocopherol | 0.1 |
| (12) purified water | balance |

(Preparation Method)

(6) and (7) were added to (12) purified water and then heated to 70 degrees centigrade. (1) to (5) were dissolved while heated, (8) to (9), (11) were then added and heated to 70 degrees centigrade, and thereafter (10) is added thereto. The latter was added to the former aqueous phase blend, emulsion particulates were homogenized by using a homogenizing mixer, then degassed, filtered, and cooled to yield cream.

Example 10

Cream

| Prescription - Blend Ratio (% by mass) | |
|---|---|
| (1) stearic acid | 5.0 |
| (2) stearyl alcohol | 4.0 |
| (3) isopropyl myristate | 18.0 |
| (4) glycerine monostearic acid ester | 3.0 |
| (5) propylene glycol | 10.0 |
| (6) phenaceturic acid | 3.0 |
| (7) potassium hydroxide | 0.2 |
| (8) potassium hydrogensulfite | 0.01 |
| (9) preservative | appropriate amount |
| (10) fragrance | appropriate amount |
| (11) ion-exchanged water | balance |

(Preparation Method)

Propylene glycol, phenaceturic acid, and potassium hydroxide are added to the ion-exchanged water, dissolved and heated to 70 degrees centigrade (aqueous phase). Other compounds were mixed, heated to dissolve, and maintained at 70 degrees centigrade (oil phase). The oil phase was gradually added to the aqueous phase to emulsify, then it was homogenized by using a homogenizing mixer to completely emulsify, and thereafter it was thoroughly stirred while being cooled to 30 degrees centigrade.

Example 11

Cream

| Prescription - Blend Ratio (% by mass) | |
|---|---|
| stearic acid | 6.0 |
| sorbitan monostearic acid ester | 2.0 |
| POE (20) sorbitan monostearic acid ester | 1.5 |
| propylene glycol | 10.0 |
| glycerine trioctanoate | 10.0 |
| squalane | 5.0 |
| N-acetyl-L-glutamic acid | 0.001 |
| sodium hydrogensulfite | 0.01 |
| ethyl paraben | 0.3 |
| fragrance | appropriate amount |
| ion-exchanged water | balance |

(Preparation Method)

Propylene glycol was added to the ion-exchanged water to dissolve, and heated to maintain at 70 degrees centigrade (aqueous phase). Other compounds were mixed, heated, and dissolved to maintain at 70 degrees centigrade (oil phase). The oil phase was added gradually to aqueous phase to preliminarily homogenize, then it was completely homogenized by using a homogenizer, and thereafter it was thoroughly stirred while being cooled to 30 degrees centigrade.

Example 12

Serum

| Prescription - Blend Ratio (% by mass) | |
| --- | --- |
| (phase A) | |
| (1) 95% ethanol | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) beta-alanine | 1.0 |
| (11) carboxyvinyl polymer | 0.2 |
| (12) purified water | balance |

(Preparation Method)

(5) methyl paraben and fragrance were added to (6) ethanol to dissolve (alcohol phase). The alcohol phase and other compounds are added to (12) purified water to dissolve and fill a bottle.

Example 13

Serum

| Prescription - Blend Ratio (% by mass) | |
| --- | --- |
| (phase A) | |
| 95% ethanol | 10.0 |
| POE (20) octyldodecanol | 1.0 |
| methyl paraben | 0.15 |
| pantotenyl ethylether | 0.1 |
| (phase B) | |
| potassium hydroxide | 0.1 |
| (phase C) | |
| glycerine | 5.0 |
| dipropylene glycol | 10.0 |
| sodium hydrogensulfite | 0.03 |
| carboxyvinyl polymer | 0.2 |
| phenaceturic acid | 2.0 |
| ion-exchanged water | balance |

(Preparation Method)

Phase A and Phase C were respectively mixed and dissolved, then phase A was added to phase C to dissolve. Then phase B was added thereto to be mixed.

Example 14

Skin Lotion

| Prescription - Blend Ratio (% by mass) | |
| --- | --- |
| (phase A) | |
| 95% ethanol | 10.0 |
| POE (20) octyldodecanol | 1.0 |
| methyl paraben | 0.15 |
| pantotenyl ethylether | 0.1 |
| (phase B) | |
| potassium hydroxide | 0.1 |
| (phase C) | |
| glycerine | 5.0 |
| dipropylene glycol | 10.0 |
| sodium hydrogensulfite | 0.03 |
| carboxyvinyl polymer | 0.2 |
| sarcosine | 3.0 |
| glycylglycine | 2.0 |
| ion-exchanged water | balance |

(Preparation Method)

Phase A and Phase C were respectively mixed and dissolved, then phase A was added to phase C to dissolve. Then phase B was added thereto to be mixed.

Example 15

Milky Lotion

| Prescription - Blend Ratio (% by mass) | |
| --- | --- |
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) PEG1500 | 3.0 |
| (7) triethanolamine | 1.0 |
| (8) sarcosine | 1.0 |
| (9) sodium hydrogensulfite | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved in a small amount of ion-exchanged water (phase A). PEG1500, sarcosine, and triethanolamine are added to the remainder of the ion-exchanged water, heated and dissolved to maintain at 70 degrees centigrade (aqueous phase). Other compounds were mixed, heated and dissolved to maintain at 70 degrees centigrade (oil phase). The oil phase was added to the aqueous phase to preliminarily homogenize, then phase A was added thereto to be completely homogenized by using a homogenizer, and thereafter it was thoroughly stirred while being cooled to 30 degrees centigrade.

Example 16

Milky Lotion

| Prescription - Blend Ratio (% by mass) | |
| --- | --- |
| (1) stearic acid | 2.5 |
| (2) cetyl-alcohol | 1.5 |
| (3) Vaseline | 5.0 |
| (4) liquid petrolatum | 10.0 |
| (5) POE (10) monooleic acid ester | 2.0 |
| (6) PEG1500 | 3.0 |
| (7) triethanolamine | 1.0 |
| (8) glycylglycine | 0.5 |
| (9) sodium hydrogensulfite | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). PEG1500, glycylglycine, and triethanolamine were added to the remainder of ion-exchanged water, heated and dissolved to maintain at 70 degrees centigrade (aqueous phase). Other compounds were mixed, heated and dissolved to maintain at 70 degrees centigrade (oil phase). The oil phase was added to the aqueous phase to preliminarily homogenize, then phase A was added thereto to be completely emulsified by using a homogenizer, and thereafter it was thoroughly stirred while being cooled to 30 degrees centigrade.

Example 17

Gel

| Prescription - Blend Ratio (% by mass) | |
| --- | --- |
| (1) 95% ethanol | 10.0 |
| (2) dipropylene glycol | 15.0 |
| (3) POE (15) oleyl alcohol ether | 2.0 |
| (4) sarcosine | 0.5 |
| (5) sodium hydrogensulfite | 0.03 |
| (6) beta-alanine ethylester hydrochloride salt | 0.5 |
| (7) carboxyvinyl polymer (Carbopole 941) | 1.0 |
| (8) caustic potash | 0.15 |
| (9) L-arginine | 0.1 |
| (10) fragrance | appropriate amount |
| (11) preservative | appropriate amount |
| (12) purified water | balance |

(Preparation Method)

(4) and (7) were homogeneously dissolved into (12) purified water (aqueous phase). (2), (3), (5), (6), (10) were dissolved into (1), then added to the aqueous phase. (8) and (9) were used to neutralize and thicken to yield gelly.

Example 18

Gel

| Prescription - Blend Ratio (% by mass) | |
| --- | --- |
| (1) 95% ethanol | 10.0 |
| (2) dipropylene glycol | 15.0 |
| (3) POE (50) oleylether | 2.0 |
| (4) carboxyvinyl polymer | 1.0 |
| (5) sodium hydroxide | 0.15 |
| (6) glycylglycine | 1.0 |
| (7) N-acetyl-L-glutamic acid | 1.0 |
| (8) methyl paraben | 0.2 |
| (9) fragrance | appropriate amount |
| (10) ion-exchanged water | balance |

(Preparation Method)

Carboxyvinyl polymer was homogeneously dissolved into the ion-exchanged water (phase A). Glycylglycine, N-acetyl-L-glutamic acid and POE (50) oleylether were dissolved into 95% ethanol then added to the phase A. Other compounds except for sodium hydroxide were added thereto, and then the sodium hydroxide was added to neutralize and thicken.

Example 19

Pack

| Prescription-Blend Ratio (% by mass) | |
| --- | --- |
| (phase A) | |
| dipropylene glycol | 5.0 |
| POE (60) hardened castor oil | 5.0 |
| (phase B) | |
| olive oil | 5.0 |
| tocopherol acetate | 0.2 |
| ethyl paraben | 0.2 |
| fragrance | 0.2 |
| (phase C) | |
| sarcosine | 1.0 |
| sodium hydrogensulfite | 0.03 |
| polyvinyl alcohol (saponified degree 90, polymerization degree 2000) | 13.0 |
| ethanol | 7.0 |
| ion-exchanged water | balance |

(Preparation Method)

Phases A, B, C were homogeneously dissolved, and phase B was added to phase A to make it soluble. Then the mixture was added to phase C and mixed.

Dosage 20: Peel-Off Type Pack

| Prescription - Blend Ratio (% by mass) | |
| --- | --- |
| (alcohol phase) | |
| 95% ethanol | 10.0 |
| POE (15) oleyl alcohol ether | 2.0 |
| preservative | appropriate amount |
| fragrance | appropriate amount |
| (aqueous phase) | |
| glycylglycine | 0.5 |
| glutathione | 3.0 |
| arbutin | 3.0 |
| polyvinyl alcohol | 12.0 |
| PEG1500 | 1.0 |
| ion-exchanged water | balance |

(Preparation Method)

The aqueous phase was prepared at 80 degrees centigrade and cooled to 50 degrees centigrade. Then, alcohol phase, prepared at the room temperature, was added thereto, homogeneously mixed and stood to cool.

Example 21

Peel-Off Type Pack

| Prescription - Blend Ratio (% by mass) | |
|---|---|
| (alcohol phase) | |
| 95% ethanol | 10.0 |
| POE (15) oleyl alcohol ether | 2.0 |
| preservative | appropriate amount |
| fragrance | appropriate amount |
| (aqueous phase) | |
| phenaceturic acid | 1.0 |
| polyvinyl alcohol | 12.0 |
| PEG1500 | 1.0 |
| ion-exchanged water | balance |

(Preparation Method)

The aqueous phase was prepared at 80 degrees centigrade and cooled to 50 degrees centigrade. Then the alcohol phase, prepared at the room temperature was added, homogeneously mixed and cooled.

Example 22

Powdered Pack

| Prescription - Blend Ratio (% by mass) | |
|---|---|
| (alcohol phase) | |
| 95% ethanol | 2.0 |
| preservative | appropriate amount |
| fragrance | appropriate amount |
| colorant | appropriate amount |
| (aqueous phase) | |
| sarcosine | 1.0 |
| propylene glycol | 7.0 |
| zinc oxide | 25.0 |
| kaolin | 20.0 |
| ion-exchanged water | balance |

(Preparation Method)

The aqueous phase was homogeneously prepared at the room temperature. Then the alcohol phase, prepared at the room temperature, is added and homogeneously mixed.

Example 23

Powdered Pack

| Prescription - Blend Ratio (% by mass) | |
|---|---|
| (alcohol phase) | |
| 95% ethanol | 2.0 |
| preservative | appropriate amount |
| fragrance | appropriate amount |
| colorant | appropriate amount |
| (aqueous phase) | |
| glycylglycine | 0.2 |
| propylene glycol | 7.0 |
| zinc oxide | 25.0 |
| kaolin | 20.0 |
| ion-exchanged water | balance |

(Preparation Method)

The aqueous phase was homogeneously prepared at the room temperature. Then the alcohol phase, prepared at the room temperature, is added and homogeneously mixed.

Example 24

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |
| (9) sarcosine | 1.0 |
| (10) liquid petrolatum | balance |
| (11) glycerine triisooctanoic acid | 15.0 |
| (12) sorbitan sesquioleic acid | 1.5 |
| (13) preservative | appropriate amount |
| (14) fragrance | appropriate amount |

(Preparation Method)

Compounds (1)-(8) were mixed and milled, then compounds (9)-(14) were mixed and added thereto, stirred and mixed, formed by a container to yield a solid foundation.

Example 25

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |

| Prescription - Blend Ratio (% by mass) | |
|---|---|
| (9) glycylglycine | 1.0 |
| (10) liquid petrolatum | balance |
| (11) glycerine triisooctanic acid | 15.0 |
| (12) sorbitan sesquioleic acid | 1.5 |
| (13) preservative | appropriate amount |
| (14) fragrance | appropriate amount |

(Preparation Method)

After mixing and grinding (1)-(8), (9)-(14) were mixed, added thereto and stirred to mix, then to formed by a container to yield a solid foundation.

Example 26

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |
| (9) phenaceturic acid | 1.0 |
| (10) N-acetyl-L-glutamic acid | 1.0 |
| (11) liquid petrolatum | balance |
| (12) glycerine triisooctanic acid | 15.0 |
| (13) sorbitan sesquioleic acid | 1.5 |
| (14) preservative | appropriate amount |
| (15) fragrance | appropriate amount |

(Preparation Method)

After mixing and grinding (1)-(8), (9)-(15) were mixed, added thereto and stirred to mix, then formed by a container to yield a solid foundation.

Example 27

Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) glycylglycine | 2.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

(9)-(15) were mixed to homogeneously dissolved, then (1)-(7) mixed and ground were added to disperse therein. (8) was added to this disperse emulsion to emulsify, then fill in a container to yield a water-in-oil emulsion type foundation.

Dosage 28: Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) N-acetyl-L-glutamic acid | 2.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

(9)-(15) were mixed to be homogeneously dissolved, then (1)-(7) mixed and ground were added to be dispersed therein. (8) was added to this disperse emulsion to emulsify, then fill in a container to yield a water-in-oil emulsion type foundation.

Example 29

Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) sarcosine | 3.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

(9)-(15) were mixed to homogeneously dissolved, then (1)-(7) having mixed and ground were added to be dispersed therein. (8) was added to this disperse emulsion to emulsify, then fill in a container to yield a water-in-oil emulsion type foundation.

Some exemplary dosages of skin preparation for external use in accordance with the invention 2 will be described herein below. Any of following dosages has an excellent effectivity of parakeratosis inhibition, pore-shrinking, skin roughness prevention/amelioration.

Example 30

Skin Lotion

| Prescription - Blend Ratio (% by mass) | |
| --- | --- |
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl alcohol ester | 0.5 |
| (6) ethanol | 10.0 |
| (7) N-ethylglycine | 3.0 |
| (8) purified water | balance |

(Preparation Method)

(1) and (2) were dissolved into (8) purified water at the room temperature to make aqueous phase. Other compounds were dissolved into (6) ethanol, then added and dissolved into the aqueous phase. Then (7) N-ethylglycine was added. The product was filtered, and filled in a bottle to yield a skin lotion.

Example 31

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) lauryl ether | 0.5 |
| (5) preservative | appropriate amount |
| (6) fragrance | appropriate amount |
| (aqueous phase) | |
| (7) 1,3-butylene glycol | 6.0 |
| (8) N-phenylglycine | 3.0 |
| (9) glycerine | 4.0 |
| (10) ion-exchanged water | balance |

(Preparation Method)

The aqueous phase and alcohol phase were separately prepared, then were mixed.

Example 32

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) hydantoic acid | 1.0 |
| (9) glycerine | 4.0 |
| (10) ion-exchanged water | balance |

(Preparation Method)

The aqueous phase and alcohol phase were separately prepared, then were mixed.

Example 33

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) glycyl-sarcosine | 5.0 |
| (9) glycerine | 4.0 |
| (10) ion-exchanged water | balance |

(Preparation Method)

The aqueous phase and alcohol phase were separately prepared, then were mixed.

Example 34

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) N-nicotinoylglycine | 0.01 |
| (9) N-phenylglycine | 0.01 |
| (10) glycerine | 4.0 |
| (11) ion-exchanged water | balance |

(Preparation Method)

The aqueous phase and alcohol phase were separately prepared, then were mixed.

Example 35

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) N-ethylglycine | 20.0 |
| (9) glycerine | 4.0 |
| (10) ion-exchanged water | balance |

(Preparation Method)

The aqueous phase and alcohol phase were separately prepared, then were mixed.

Example 36

Skin Lotion

| Prescription-Blend Ratio (% by mass) | |
| --- | --- |
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl alcohol ester | 0.5 |
| (6) ethanol | 10.0 |
| (7) hydantoic acid | 1.0 |
| (8) N-ethylglycine | 1.0 |
| (9) N-(2-hydroxyethyl)ethylenediamine triacetate | 0.2 |
| (10) purified water | balance |

(Preparation Method)

(1) and (2) were dissolved in (10) purified water at the room temperature to make aqueous phase. Other compounds were dissolved in (6) ethanol, then added to and mixed with the aqueous phase. Thereafter, (7) hydantoic acid and (8) N-ethylglycine were added thereto. The product was filtered and filled in a bottle to yield a skin lotion.

Example 37

Cream

| Prescription-Blend Ratio (% by mass) | |
| --- | --- |
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) PEG1500 | 4.0 |
| (8) POE (25) cetyl-alcohol ester | 3.0 |
| (9) glycerine monostearate | 2.0 |
| (10) N-ethylglycine | 0.2 |
| (11) tocopherol | 0.1 |
| (12) purified water | balance |

(Preparation Method)

(6) and (7) were added to (12) purified water and heated to 70 degrees centigrade to prepare aqueous phase. (1) to (5) were heated to melt, then (8), (9), (11) were added thereto and heated to 70 degrees centigrade. (10) was then added thereto. The product was added to the aqueous phase, emulsified with a homogenizer to uniformly homogenize the particulates, thereafter degassed, filtered, cooled to yield cream.

Example 38

Cream

| Prescription-Blend Ratio (% by mass) | |
| --- | --- |
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) PEG1500 | 4.0 |
| (8) POE (25) cetyl alcohol ester | 3.0 |
| (9) glycerine monostearate | 2.0 |
| (10) glycylglycine ethylester hydrochloride | 10.0 |
| (11) tocopherol | 0.1 |
| (12) purified water | balance |

(Preparation Method)

(6) and (7) were added to (12) purified water and heated to 70 degrees centigrade to prepare aqueous phase. After (1) to (5) are heated to melt, (8), (9), (11) were added thereto and heated to 70 degrees centigrade. Then (10) was added. The product was added to the aqueous phase, emulsified with a homogenizer to homogenize the particulates, then degassed, filtered, and cooled to yield cream.

Example 39

Cream

| Prescription-Blend Ratio (% by mass) | |
| --- | --- |
| (1) stearic acid | 5.0 |
| (2) stearyl alcohol | 4.0 |
| (3) isopropyl myristate | 18.0 |
| (4) glycerine monostearic acid ester | 3.0 |
| (5) propylene glycol | 10.0 |
| (6) hydantoic acid | 3.0 |
| (7) potassium hydroxide | 0.2 |
| (8) sodium hydrogensulfite | 0.01 |
| (9) preservative | appropriate amount |
| (10) fragrance | appropriate amount |
| (11) ion-exchanged water | balance |

(Preparation Method)

Propylene glycol, hydantoic acid, and potassium hydroxide are added to the ion-exchanged water, dissolved and heated to maintain at 70 degrees centigrade (aqueous phase). Other compounds were mixed, heated to melt and maintained at 70 degrees centigrade (oil phase). The oil phase was gradually added to the aqueous phase to preliminarily emulsify, then completely emulsified with a homogenizer, thoroughly stirred while being cooled to 30 degrees centigrade.

Example 40

Cream

| Prescription-Blend Ratio (% by mass) | |
| --- | --- |
| stearic acid | 6.0 |
| sorbitan monostearic acid ester | 2.0 |
| POE (20) sorbitan monostearic acid ester | 1.5 |
| propylene glycol | 10.0 |
| glycerine trioctanoate | 10.0 |
| squalane | 5.0 |
| glycyl sarcosine ethylester hydrochloride salt | 0.001 |
| sodium hydrogensulfate | 0.01 |
| ethyl paraben | 0.3 |
| fragrance | appropriate amount |
| ion-exchanged water | balance |

(Preparation Method)

Propylene glycol was added into ion-exchanged water to dissolve, then heated to maintain at 70 degrees centigrade (aqueous phase). Other compounds were mixed, heated to melt and maintained at 70 degrees centigrade (oil phase). The oil phase was gradually added to the aqueous phase to preliminarily emulsify, then completely emulsified with a homogenizer, and sufficiently stirred while being cooled at 30 degrees centigrade.

Example 41

Serum

| Prescription-Blend Ratio (% by mass) | |
| --- | --- |
| (phase A) | |
| (1) ethyl alcohol (95%) | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) N-ethylglycine | 1.0 |
| (11) carboxyvinyl polymer | 0.2 |
| (12) purified water | balance |

(Preparation Method)

Phases A and C were respectively homogeneously dissolved, then phase A was added to phase C to make it soluble. Then phase B was added thereto and mixed.

Example 42

Serum

| Prescription-Blend Ratio (% by mass) | |
| --- | --- |
| (phase A) | |
| (1) 95% ethanol | 10.0 |
| (2) POE (20) octyldodecanol | 1.0 |
| (3) methyl paraben | 0.15 |
| (4) pantotenyl ethylether | 0.1 |
| (phase B) | |
| (5) potassium hydroxide | 0.1 |
| (phase C) | |
| (6) glycerine | 5.0 |
| (7) dipropylene glycol | 10.0 |
| (8) sodium hydrogensulfate | 0.03 |
| (9) carboxyvinyl polymer | 0.2 |
| (10) hydantoic acid | 2.0 |
| (11) ion-exchanged water | balance |

(Preparation Method)

Phases A and C were respectively dissolved, then phase A was added to phase C to make it soluble. Then phase B was added thereto and mixed.

Example 43

Serum

| Prescription-Blend Ratio (% by mass) | |
| --- | --- |
| (phase A) | |
| 95% ethanol | 10.0 |
| POE (20) octyldodecanol | 1.0 |
| methyl paraben | 0.15 |
| pantotenyl ethylether | 0.1 |
| (phase B) | |
| potassium hydroxide | 0.1 |
| (phase C) | |
| glycerine | 5.0 |
| dipropylene glycol | 10.0 |
| sodium hydrogensulfate | 0.03 |
| carboxyvinyl polymer | 0.2 |
| N-phenylglycine | 3.0 |
| L-aminocyclohexane carbonate | 2.0 |
| ion-exchanged water | balance |

(Preparation Method)

Phases A and C were respectively dissolved, then phase A was added to phase C to make it soluble. Then phase B was added thereto and mixed.

Example 44

Milky Lotion

| Prescription-Blend Ratio (% by mass) | |
|---|---|
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) PEG1500 | 3.0 |
| (7) triethanolamine | 1.0 |
| (8) hydantoic acid | 1.0 |
| (9) sodium hydrogensulfate | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). To the remainder of ion-exchanged water, PEG1500, hydantoic acid, and triethanolamine were added, heat to dissolve, and maintained at 70 degrees centigrade (aqueous phase). Other compounds were mixed, heated to melt and maintained at 70 degrees centigrade (oil phase). The oil phase was added to the aqueous phase to preliminarily emulsify, then phase A was added thereto, completely emulsified, and then stirred while being cooled to 30 degrees centigrade.

Example 45

Milky Lotion

| Prescription-Blend Ratio (% by mass) | |
|---|---|
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) POE1500 | 3.0 |
| (7) triethanolamine | 1.0 |
| (8) N-ethylglycine | 0.5 |
| (9) sodium hydrogensulfate | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). To the remainder of ion-exchanged water, PEG1500, N-ethylglycine, and triethanolamine were added, heat to dissolve, and maintained at 70 degrees centigrade (aqueous phase). Other compounds were mixed, heated to melt and maintained at 70 degrees centigrade (oil phase). The oil phase was added to the aqueous phase to preliminarily emulsify, then phase A was added thereto, completely emulsified, and then stirred while being cooled to 30 degrees centigrade.

Example 46

Gel

| Prescription - Blend Ratio (% by mass) | |
|---|---|
| (1) 95% ethanol | 10.0 |
| (2) dipropylene glycol | 15.0 |
| (3) POE (15) oleyl alcohol ether | 2.0 |
| (4) N-ethylglycine | 0.5 |
| (5) sodium hydrogensulfate | 0.03 |
| (6) hydantoic acid | 0.5 |
| (7) carboxyvinyl polymer (Carbopole 941) | 1.0 |
| (8) caustic potash | 0.15 |
| (9) L-arginine | 0.1 |
| (10) fragrance | appropriate amount |
| (11) preservative | appropriate amount |
| (12) purified water | balance |

(Preparation Method)

(4) and (7) were homogeneously dissolved in (12) purified water (aqueous phase). Separately, (2), (3), (5), (6), (10), (11) are dissolved into (1), then added to the aqueous phase. Next, (8) and (9) are used to neutralize and thicken to yield gelly.

Example 47

Gel

| Prescription - Blend Ratio (% by mass) | |
|---|---|
| (1) 95% ethanol | 10.0 |
| (2) dipropylene glycol | 15.0 |
| (3) POE (50) oleylether | 2.0 |
| (4) carboxyvinyl polymer | 1.0 |
| (5) sodium hydroxide | 0.15 |
| (6) N-phenylglycine | 1.0 |
| (7) glycyl sarcosine | 1.0 |
| (8) methyl paraben | 0.2 |
| (9) fragrance | appropriate amount |
| (10) ion-exchanged water | balance |

(Preparation Method)

Carboxyvinyl polymer was homogeneously dissolved in the ion-exchanged water (phase A). N-phenylglycine, glycyl sarcosine, POE (50) oleylether were dissolved in 95% ethanol, then added to phase A. After other compounds except for sodium hydroxide was added, sodium hydroxide was added to neutralize and thicken.

Example 48

Pack

| Prescription - Blend Ratio (% by mass) | |
|---|---|
| (phase A) | |
| dipropylene glycol | 5.0 |
| POE (60) hardened castor oil | 5.0 |
| (phase B) | |
| olive oil | 5.0 |
| tocopherol acetate | 0.2 |

-continued

| Prescription - Blend Ratio (% by mass) | |
|---|---|
| ethyl paraben | 0.2 |
| fragrance | 0.2 |
| (phase C) | |
| N-ethylglycine | 1.0 |
| sodium hydrogensulfate | 0.03 |
| polyvinyl alcohol | 13.0 |
| (saponified degree 90, polymerization degree 2000) | |
| ethanol | 7.0 |
| ion-exchanged water | balance |

(Preparation Method)

Phases A, B, and C were separately homogeneously dissolved, then phase B was added to phase A to make it soluble. Thereafter, the product is added to phase C to mix.

Example 49

Peel-Off Type Pack

| Prescription - Blend Ratio (% by mass) | |
|---|---|
| (alcohol phase) | |
| 95% ethanol | 10.0 |
| POE (15) oleyl alcohol ether | 2.0 |
| preservative | appropriate amount |
| fragrance | appropriate amount |
| (aqueous phase) | |
| hydantoic acid | 0.5 |
| glutathione | 3.0 |
| arbutin | 3.0 |
| polyvinyl alcohol | 12.0 |
| PEG1500 | 1.0 |
| ion-exchanged water | balance |

(Preparation Method)

Aqueous phase was prepared at 80 degrees centigrade, then cooled to 50 degrees centigrade. Next, alcohol phase, prepared at the room temperature, was added thereto, homogeneously mixed, and stood to cool.

Example 50

Peel-Off Type Pack

| Prescription - Blend Ratio (% by mass) | |
|---|---|
| (alcohol phase) | |
| 95% ethanol | 10.0 |
| POE (15) oleyl alcohol ether | 2.0 |
| preservative | appropriate amount |
| fragrance | appropriate amount |
| (aqueous phase) | |
| 1-aminocyclohexane carbonate | 1.0 |
| polyvinyl alcohol | 12.0 |
| PEG1500 | 1.0 |
| ion-exchanged water | balance |

(Preparation Method)

Aqueous phase was prepared at 80 degrees centigrade, then cooled to 50 degrees centigrade. Next, alcohol phase, prepared at the room temperature, was added thereto, homogeneously mixed, and stood to cool.

Example 51

Powdered Pack

| Prescription - Blend Ratio (% by mass) | |
|---|---|
| (alcohol phase) | |
| 95% ethanol | 2.0 |
| preservative | appropriate amount |
| fragrance | appropriate amount |
| colorant | appropriate amount |
| (aqueous phase) | |
| N-ethylglycine | 1.0 |
| propylene glycol | 7.0 |
| zinc oxide | 25.0 |
| kaolin | 20.0 |
| ion-exchanged water | balance |

(Preparation Method)

Aqueous phase was homogeneously prepared at the room temperature. Then alcohol phase, prepared at the room temperature, is added thereto to homogeneously mix.

Example 52

Powdered Pack

| Prescription - Blend Ratio (% by mass) | |
|---|---|
| (alcohol phase) | |
| 95% ethanol | 2.0 |
| preservative | appropriate amount |
| fragrance | appropriate amount |
| colorant | appropriate amount |
| (aqueous phase) | |
| hydantoic acid | 0.2 |
| propylene glycol | 7.0 |
| zinc oxide | 25.0 |
| kaolin | 20.0 |
| ion-exchanged water | balance |

(Preparation Method)

Aqueous phase was homogeneously prepared at the room temperature. Then alcohol phase, prepared at the room temperature, is added thereto to homogeneously mix.

Example 53

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |

-continued

| Prescription - Blend Ratio (% by mass) | |
|---|---|
| (6) titanium dioxide | 5.0 |
| (7) iron oxide | 3.0 |
| (8) zinc stearate | 5.0 |
| (9) N-ethylglycine | 1.0 |
| (10) liquid petrolatum | balance |
| (11) glycerine triisooctanic acid | 15.0 |
| (12) sorbitan sesqui-oleic acid | 1.5 |
| (13) preservative | appropriate amount |
| (14) fragrance | appropriate amount |

(Preparation Method)

(1) to (8) were mixed and ground. Other compounds (9) to (14) are mixed and added, then stirred to mix, and formed by a container to yield a solid foundation.

Example 54

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |
| (9) hydantoic acid | 1.0 |
| (10) liquid petrolatum | balance |
| (11) glycerine triisooctanic acid | 15.0 |
| (12) sorbitan sesqui-oleic acid | 1.5 |
| (13) preservative | appropriate amount |
| (14) fragrance | appropriate amount |

(Preparation Method)

(1) to (8) were mixed and ground. Other compounds (9) to (14) are mixed and added, then stirred to mix, and formed by a container to yield a solid foundation.

Example 55

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |
| (9) N-phenylglycine | 1.0 |
| (10) N-nicotinoylglycine | 1.0 |
| (11) liquid petrolatum | balance |
| (12) glycerine triisooctanic acid | 15.0 |
| (13) sorbitan sesqui-oleic acid | 1.5 |
| (14) preservative | appropriate amount |
| (15) fragrance | appropriate amount |

(Preparation Method)

(1) to (8) were mixed and ground. Other compounds (9) to (15) are mixed and added, then stirred to mix, and formed by a container to yield a solid foundation.

Example 56

Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) N-ethylglycine | 2.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

Compounds (9) to (15) were mixed to homogeneously dissolved, then (1) to (7) having mixed and ground were added thereto to disperse. This suspension was added with (8) to emulsify, then fill in a bottle to yield a water-in-oil emulsion type foundation.

Example 57

Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) hydantoic acid | 2.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

(9)-(15) were mixed to homogeneously dissolved, then (1)-(7) having mixed and ground were added to disperse therein. (8) was added to this disperse emulsion to emulsify, then fill in a container to yield a water-in-oil emulsion type foundation.

Example 58

Water-In-Oil Emulsion Type Foundation

| Prescription - Blend Ratio (% by mass) | |
| --- | --- |
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) 1-aminocyclohexane carbonic acid | 3.0 |
| (10) decamethylcyclopentane siloxane | 18.0 |
| (11) dimethylpolysiloxane | 5.0 |
| (12) squalane | 1.0 |
| (13) POE denatured dimethylpolysiloxane | 2.0 |
| (14) preservative | appropriate amount |
| (15) fragrance | appropriate amount |

(Preparation Method)

(9)-(15) were mixed to homogeneously dissolved, then (1)-(7) having mixed and ground were added to disperse therein. (8) was added to this disperse emulsion to emulsify, then fill in a container to yield a water-in-oil emulsion type foundation.

Example 59

Skin Lotion

| Prescription - Blend Ratio (% by mass) | |
| --- | --- |
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl-alcohol ester | 0.5 |
| (6) ethanol | 10.0 |
| (7) CAPS | 3.0 |
| (8) purified water | balance. |

(Preparation Method)

(1) and (2) were dissolved to (8) purified water at room temperature to yield aqueous phase. Other compounds were dissolved to (6) ethanol to make solvable into the aqueous phase above. Then (7) CAPS was added thereto. Thereafter, the product was filtered and filled in a bottle to obtain a lotion.

Example 60

Skin Lotion

| Prescription - Blend Ratio (% by mass) | |
| --- | --- |
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl-alcohol ester | 0.5 |
| (6) ethanol | 10.0 |
| (7) CAPSO | 3.0 |
| (8) purified water | balance. |

(Preparation Method)

(1) and (2) were dissolved to (8) purified water at room temperature to yield aqueous phase. Other compounds were dissolved to (6) ethanol to make solvable into the aqueous phase above. Then (7) CAPSO was added thereto. Thereafter, the product was filtered and filled in a bottle to obtain a lotion.

Example 61

Skin Lotion

| Prescription - Blend Ratio (% by mass) | |
| --- | --- |
| (1) 1,3-butylene glycol | 6.0 |
| (2) glycerine | 4.0 |
| (3) oleyl alcohol | 0.1 |
| (4) POE (20) sorbitan monolauric acid ester | 0.5 |
| (5) POE (15) lauryl-alcohol ester | 0.5 |
| (6) ethanol | 3.0 |
| (7) ACES | 2.0 |
| (8) purified water | balance. |

(Preparation Method)

(1) and (2) were dissolved to (8) purified water at room temperature to yield aqueous phase. Other compounds were dissolved to (6) ethanol to make solvable into the aqueous phase above. Then (7) ACES was added thereto. Thereafter, the product was filtered and filled in a bottle to obtain a lotion.

Example 62

Skin Lotion

| | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) ACES | 1.0 |
| (9) glycerine | 4.0 |
| (10) ion-exchanged water | balance |

(Preparation Method)

The aqueous phase and alcohol phase were separately prepared, then were mixed.

Example 63

Skin Lotion

| Prescription - Blend Ratio (% by mass) | |
| --- | --- |
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) CAPS | 3.0 |
| (9) glycerine | 4.0 |
| (10) ion-exchanged water | balance |

(Preparation Method)

The aqueous phase and alcohol phase were separately prepared, then were mixed.

Example 64

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) CAPSO | 3.0 |
| (9) glycerine | 4.0 |
| (10) ion-exchanged water | balance |

(Preparation Method)

The aqueous phase and alcohol phase were separately prepared, then were mixed.

Example 65

Skin Lotion

| Prescription - Blend Ratio (% by mass) | |
|---|---|
| (alcohol phase) | |
| (1) ethanol | 10.0 |
| (2) oleyl alcohol | 0.1 |
| (3) POE (20) sorbitan monolauric acid ester | 0.5 |
| (4) POE (15) laurylether | 0.5 |
| (5) preservative | appropriate amount |
| (6) fragrance | appropriate amount |
| (aqueous phase) | |
| (7) 1,3-butylene glycol | 6.0 |
| (8) ACES | 3.0 |
| (9) CAPS | 3.0 |
| (10) CAPSO | 3.0 |
| (11) glycerine | 4.0 |
| (12) ion-exchanged water | balance |

(Preparation Method)

The aqueous phase and alcohol phase were separately prepared, then were mixed.

Example 66

Cream

| Prescription - Blend Ratio (% by mass) | |
|---|---|
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) polyethylene glycol 1500 | 4.0 |
| (8) POE (25) cetyl-alcohol ester | 3.0 |
| (9) glycerine monostearate | 2.0 |
| (10) ACES | 0.2 |
| (11) tocopherol | 0.1 |
| (12) purified water | balance |

(Preparation Method)

(6) and (7) were added to (12) purified water and heated to 70 degrees centigrade to prepare aqueous phase. Separately, (1) to (5) are heated to melt, then (8), (9), (11) were added thereto and heated to 70 degrees centigrade. (10) was then added thereto. The product was added to the aqueous phase, emulsified with a homogenizer to uniformly homogenize the particulates, thereafter degassed, filtered, cooled to yield cream.

Example 67

Cream

| Prescription - Blend Ratio (% by mass) | |
|---|---|
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) polyethylene glycol 1500 | 4.0 |
| (8) POE (25) cetyl-alcohol ester | 3.0 |
| (9) glycerine monostearate | 2.0 |
| (10) CAPS | 0.2 |
| (11) tocopherol | 0.1 |
| (12) purified water | balance |

(Preparation Method)

(6) and (7) were added to (12) purified water and heated to 70 degrees centigrade to prepare aqueous phase. After (1) to (5) are heated to melt, (8), (9), (11) were added thereto and heated to 70 degrees centigrade. Then (10) was added. The product was added to the aqueous phase, emulsified with a homogenizer to homogenize the particulates, then degassed, filtered, and cooled to yield cream.

Example 68

Cream

| Prescription - Blend Ratio (% by mass) | |
|---|---|
| (1) stearyl alcohol | 6.0 |
| (2) stearic acid | 2.0 |
| (3) hydrogenated lanolin | 4.0 |
| (4) squalane | 9.0 |
| (5) octyldodecanol | 10.0 |
| (6) 1,3-butylene glycol | 6.0 |
| (7) polyethylene glycol 1500 | 4.0 |
| (8) POE (25) cetyl-alcohol ester | 3.0 |
| (9) glycerine monostearate | 2.0 |
| (10) CAPSO | 0.2 |

-continued

| | |
|---|---|
| (11) tocopherol | 0.1 |
| (12) purified water | balance |

(Preparation Method)

(6) and (7) were added to (12) purified water and heated to 70 degrees centigrade to prepare aqueous phase. After (1) to (5) are heated to melt, (8), (9), (11) were added thereto and heated to 70 degrees centigrade. Then (10) was added. The product was added to the aqueous phase, emulsified with a homogenizer to homogenize the particulates, then degassed, filtered, and cooled to yield cream.

Example 69

Cream

| Prescription - Blend Ratio (% by mass) | |
|---|---|
| (1) stearic acid | 5.0 |
| (2) stearyl alcohol | 4.0 |
| (3) isopropyl myristate | 18.0 |
| (4) glycerine monostearic acid ester | 3.0 |
| (5) propylene glycol | 10.0 |
| (6) ACES | 0.3 |
| (7) potassium hydroxide | 0.2 |
| (8) sodium hydrogensulfite | 0.01 |
| (9) preservative | appropriate amount |
| (10) fragrance | appropriate amount |
| (11) ion-exchanged water | balance |

(Preparation Method)

Propylene glycol, ACES, and potassium hydroxide were added to the ion-exchanged water, dissolved and heated to maintain at 70 degrees centigrade (aqueous phase). Other compounds were mixed, heated to melt and maintained at 70 degrees centigrade (oil phase). The oil phase is gradually added to the aqueous phase to preliminarily emulsify, then completely emulsified with a homogenizer, stirred while being cooled to 30 degrees centigrade.

Example 70

Cream

| Prescription - Blend Ratio (% by mass) | |
|---|---|
| (1) stearic acid | 5.0 |
| (2) stearyl alcohol | 4.0 |
| (3) isopropyl myristate | 18.0 |
| (4) glycerine monostearic acid ester | 3.0 |
| (5) propylene glycol | 10.0 |
| (6) CAPS | 1.0 |
| (7) potassium hydroxide | 0.2 |
| (8) sodium hydrogensulfite | 0.01 |
| (9) preservative | appropriate amount |
| (10) fragrance | appropriate amount |
| (11) ion-exchanged water | balance |

(Preparation Method)

Propylene glycol, CAPS, and potassium hydroxide were added to the ion-exchanged water, dissolved and heated to maintain at 70 degrees centigrade (aqueous phase). Other compounds were mixed, heated to melt and maintained at 70 degrees centigrade (oil phase). The oil phase is gradually added to the aqueous phase to preliminarily emulsify, then completely emulsified with a homogenizer, stirred while being cooled to 30 degrees centigrade.

Example 71

Cream

| Prescription - Blend Ratio (% by mass) | |
|---|---|
| (1) stearic acid | 5.0 |
| (2) stearyl alcohol | 4.0 |
| (3) isopropyl myristate | 18.0 |
| (4) glycerine monostearic acid ester | 3.0 |
| (5) propylene glycol | 10.0 |
| (6) CAPSO | 1.0 |
| (7) potassium hydroxide | 0.2 |
| (8) sodium hydrogensulfite | 0.01 |
| (9) preservative | appropriate amount |
| (10) fragrance | appropriate amount |
| (11) ion-exchanged water | balance |

(Preparation Method)

Propylene glycol, CAPSO, and potassium hydroxide were added to the ion-exchanged water, dissolved and heated to maintain at 70 degrees centigrade (aqueous phase). Other compounds were mixed, heated to melt and maintained at 70 degrees centigrade (oil phase). The oil phase is gradually added to the aqueous phase to preliminarily emulsify, then completely emulsified with a homogenizer, stirred while being cooled to 30 degrees centigrade.

Example 72

Serum

| Prescription - Blend Ratio (% by mass) | |
|---|---|
| (phase A) | |
| (1) ethyl alcohol (95%) | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) ACES | 1.0 |
| (11) carboxyvinyl polymer | 0.2 |
| (12) purified water | balance |

(Preparation Method)

Phases A and C were respectively homogeneously molten, then phase A was added to phase C to make it soluble. Then phase B was added thereto and mixed.

Example 73

Serum

| Prescription - Blend Ratio (% by mass) | |
|---|---|
| (phase A) | |
| (1) 95% ethanol | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) CAPS | 3.0 |
| (11) carboxyvinyl polymer | 0.2 |
| (12) purified water | balance |

(Preparation Method)

Phases A and C were respectively dissolved, then phase A was added to phase C to make it soluble. Then phase B was added thereto and mixed.

Example 74

Serum

| Prescription - Blend Ratio (% by mass) | |
|---|---|
| (phase A) | |
| (1) ethyl alcohol (95%) | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) CAPSO | 3.0 |
| (11) carboxyvinyl polymer | 0.2 |
| (12) purified water | balance |

(Preparation Method)

Phases A and C were respectively homogeneously molten, then phase A was added to phase C to make it soluble. Then phase B was added thereto and mixed.

Example 75

Serum

| Prescription - Blend Ratio (% by mass) | |
|---|---|
| (phase A) | |
| (1) ethyl alcohol (95%) | 10.0 |
| (2) POE (20) octyldodecanol | 1.0 |
| (3) pantotenyl ethylether | 0.1 |
| (4) ASDA 4Na | 1.5 |
| (5) methyl paraben | 0.15 |
| (6) ethanol | 10.0 |
| (phase B) | |
| (7) potassium hydroxide | 0.1 |
| (phase C) | |
| (8) glycerine | 5.0 |
| (9) dipropylene glycol | 10.0 |
| (10) ACES | 1.0 |
| (11) CAPS | 1.0 |
| (12) CAPSO | 1.0 |
| (13) carboxyvinyl polymer | 0.2 |
| (14) purified water | balance |

(Preparation Method)

Phases A and C were respectively homogeneously dissolved, then phase A was added to phase C to make it soluble. Then phase B was added thereto and mixed.

Example 76

Milky Lotion

| Prescription - Blend Ratio (% by mass) | |
|---|---|
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) PEG1500 | 3.0 |
| (7) triethanolamine | 1.0 |
| (8) ACES | 1.0 |
| (9) sodium hydrogensulfate | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). To the remainder of ion-exchanged water, PEG1500, ACES, and triethanolamine were added, heat to dissolve, and maintained at 70 degrees centigrade (aqueous phase). Other compounds were mixed, heated to melt and maintained at 70 degrees centigrade (oil phase). The oil phase was added to the aqueous phase to preliminarily emulsify, then phase A was added thereto, completely emulsified, and then stirred while being cooled to 30 degrees centigrade.

Example 77

Milky Lotion

| | |
|---|---|
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) POE1500 | 3.0 |
| (7) triethanolamine | 1.0 |
| (8) CAPS | 1.0 |
| (9) sodium hydrogensulfate | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). To the remainder of ion-exchanged water, PEG1500, CAPS, and triethanolamine were added, heat to dissolve, and maintained at 70 degrees centigrade (aqueous phase). Other compounds are mixed, heated to melt and maintained at 70 degrees centigrade (oil phase). The oil phase was added to the aqueous phase to preliminarily emulsify, then phase A was added thereto, completely emulsified, and then stirred while being cooled to 30 degrees centigrade.

Example 78

Milky Lotion

| | |
|---|---|
| (1) stearic acid | 2.5 |
| (2) cetyl alcohol | 1.5 |
| (3) Vaseline | 5.0 |
| (4) liquid petrolatum | 10.0 |
| (5) POE (10) monooleic acid ester | 2.0 |
| (6) PEG1500 | 3.0 |
| (7) triethanolamine | 1.0 |
| (8) CAPSO | 1.0 |
| (9) sodium hydrogensulfate | 0.01 |
| (10) ethyl paraben | 0.3 |
| (11) carboxyvinyl polymer | 0.05 |
| (12) fragrance | appropriate amount |
| (13) ion-exchanged water | balance |

(Preparation Method)

Carboxyvinyl polymer was dissolved into a small amount of ion-exchanged water (phase A). To the remainder of ion-exchanged water, PEG1500, CAPSO, and triethanolamine were added, heat to dissolve, and maintained at 70 degrees centigrade (aqueous phase). Other compounds were mixed, heated to melt and maintained at 70 degrees centigrade (oil phase). The oil phase was added to the aqueous phase to preliminarily emulsify, then phase A was added thereto, completely emulsified, and then stirred while being cooled to 30 degrees centigrade.

Example 79

Gel

| Prescription - Blend Ratio (% by mass) | |
|---|---|
| (1) 95% ethanol | 10.0 |
| (2) dipropylene glycol | 15.0 |
| (3) POE (15 mol) oleyl alcohol ether | 2.0 |
| (4) ACES | 0.5 |
| (5) CAPS | 0.5 |
| (6) CAPSO | 0.5 |
| (7) sodium hydrogensulfite | 0.03 |
| (8) glycylglycine | 0.5 |
| (9) sarcosine | 0.5 |
| (10) carboxyvinyl polymer (Carbopole 941) | 1.0 |
| (11) caustic potash | 0.15 |
| (12) L-arginine | 0.1 |
| (13) fragrance | appropriate amount |
| (14) preservative | appropriate amount |
| (15) purified water | balance |

(Preparation Method)

(4), (5), (6), (8), (9), and (10) were homogeneously dissolved into (15) purified water (aqueous phase). Separately, (2), (3), (7), (13) and (14) were dissolved into (1) then added to the aqueous phase. Next, the product was neutralized by (11) and (12) to yield gel.

Example 80

Gel

| Prescription - Blend Ratio (% by mass) | |
|---|---|
| (1) 95% ethanol | 10.0 |
| (2) dipropylene glycol | 15.0 |
| (3) POE (50) oleylether | 2.0 |
| (4) carboxyvinyl polymer | 1.0 |
| (5) sodium hydroxide | 0.15 |
| (6) ACES | 1.0 |
| (7) methyl paraben | 0.2 |
| (8) fragrance | appropriate amount |
| (9) ion-exchanged water | balance |

(Preparation Method)

Carboxyvinyl polymer was homogeneously dissolved into the ion-exchanged water (phase A). ACES and POE (50) oleylether are dissolved into 95% ethanol and added to phase A. Other compounds except for sodium hydroxide were added thereto, thereafter the sodium hydroxide is added to neutralize and thicken.

Dosage 81: Gel

| Prescription - Blend Ratio (% by mass) | |
|---|---|
| (1) 95% ethanol | 10.0 |
| (2) dipropylene glycol | 15.0 |
| (3) POE (50) oleylether | 2.0 |
| (4) carboxyvinyl polymer | 1.0 |
| (5) sodium hydroxide | 0.15 |
| (6) CAPS | 1.0 |
| (7) methyl paraben | 0.2 |
| (8) fragrance | appropriate amount |
| (9) ion-exchanged water | balance |

(Preparation Method)

Carboxyvinyl polymer was homogeneously dissolved in the ion-exchanged water (phase A). CAPS and POE (50) oleylether are dissolved in 95% ethanol, then added to phase A. Other compounds except for sodium hydroxide were added, thereafter sodium hydroxide was added to neutralize and thicken.

Example 82

Gel

| Prescription - Blend Ratio (% by mass) | |
|---|---|
| (1) 95% ethanol | 10.0 |
| (2) dipropylene glycol | 15.0 |
| (3) POE (50) oleylether | 2.0 |
| (4) carboxyvinyl polymer | 1.0 |
| (5) sodium hydroxide | 0.15 |
| (6) CAPSO | 1.0 |
| (7) methyl paraben | 0.2 |
| (8) fragrance | appropriate amount |
| (9) ion-exchanged water | balance |

(Preparation Method)

Carboxyvinyl polymer was homogeneously dissolved in the ion-exchanged water (phase A). CAPSO and POE (50) oleylether are dissolved in 95% ethanol, then added to phase A. After other compounds except for sodium hydroxide were added, sodium hydroxide was added to neutralize and thicken.

Example 83

Pack

| Prescription - Blend Ratio (% by mass) | |
|---|---|
| (phase A) | |
| dipropylene glycol | 5.0 |
| POE (60) hardened castor oil | 5.0 |
| (phase B) | |
| olive oil | 5.0 |
| tocopherol acetate | 0.2 |
| ethyl paraben | 0.2 |
| fragrance | 0.2 |
| (phase C) | |
| ACES | 1.0 |
| sodium hydrogensulfate | 0.03 |
| polyvinyl alcohol | 13.0 |
| (saponified degree 90, polymerization degree 2000) | |
| ethanol | 7.0 |
| ion-exchanged water | balance |

(Preparation Method)

Phases A, B, and C were separately homogeneously dissolved, then phase B was added to phase A to make it soluble. Thereafter, the product is added to phase C to be mixed.

Example 84

Pack

| Prescription - Blend Ratio (% by mass) | |
|---|---|
| (phase A) | |
| dipropylene glycol | 5.0 |
| POE (60) hardened castor oil | 5.0 |
| (phase B) | |
| olive oil | 5.0 |
| tocopherol acetate | 0.2 |
| ethyl paraben | 0.2 |
| fragrance | 0.2 |
| (phase C) | |
| CAPS | 1.0 |
| sodium hydrogensulfate | 0.03 |
| polyvinyl alcohol | 13.0 |
| (saponified degree 90, polymerization degree 2000) | |
| ethanol | 7.0 |
| ion-exchanged water | balance |

(Preparation Method)

Phases A, B, and C were separately homogeneously dissolved, then phase B was added to phase A to make it soluble. Thereafter, the product is added to phase C to be mixed.

Dose 85: Pack

| Prescription - Blend Ratio (% by mass) | |
|---|---|
| (phase A) | |
| dipropylene glycol | 5.0 |
| POE (60) hardened castor oil | 5.0 |
| (phase B) | |
| olive oil | 5.0 |
| tocopherol acetate | 0.2 |
| ethyl paraben | 0.2 |
| fragrance | 0.2 |
| (phase C) | |
| CAPSO | 1.0 |
| sodium hydrogensulfate | 0.03 |
| polyvinyl alcohol | 13.0 |
| (saponified degree 90, polymerization degree 2000) | |
| ethanol | 7.0 |
| ion-exchanged water | balance |

(Preparation Method)

Phases A, B, and C were separately homogeneously dissolved, then phase B was added to phase A to make it soluble. Thereafter, the product is added to phase C to be mixed.

Example 86

Peel-Off Type Pack

| (alcohol phase) | |
|---|---|
| 95% ethanol | 10.0 |
| POE (15 mol) oleyl alcohol ether | 2.0 |
| preservative | appropriate amount |
| fragrance | appropriate amount |
| (aqueous phase) | |
| ACES | 0.5 |
| CAPS | 0.5 |
| CAPSO | 0.5 |
| glutathione | 3.0 |

-continued

| | |
|---|---|
| arbutin | 3.0 |
| polyvinyl alcohol | 12.0 |
| polyethylene glycol 1500 | 1.0 |
| ion-exchanged water | balance |

(Preparation Method)

Aqueous phase was prepared at 80 degrees centigrade, then cooled to 50 degrees centigrade. Next, alcohol phase, prepared at the room temperature, was added thereto, homogeneously mixed, and stood to cool.

Example 87

Powdered Pack

| Prescription - Blend Ratio (% by mass) | |
|---|---|
| (alcohol phase) | |
| 95% ethanol | 2.0 |
| preservative | appropriate amount |
| fragrance | appropriate amount |
| colorant | appropriate amount |
| (aqueous phase) | |
| ACES | 0.5 |
| CAPS | 1.0 |
| CAPSO | 1.0 |
| propylene glycol | 7.0 |
| zinc oxide | 25.0 |
| kaolin | 20.0 |
| ion-exchanged water | balance |

(Preparation Method)

Aqueous phase was homogeneously prepared at the room temperature. Then alcohol phase, prepared at the room temperature, is added thereto to be homogeneously mixed.

Example 88

Solid Powdery Foundation

| Prescription - Blend Ratio (% by mass) | |
|---|---|
| (1) talc | 15.0 |
| (2) sericite | 10.0 |
| (3) spherical nylon powder | 10.0 |
| (4) porous unhydride silicic acid powder | 15.0 |
| (5) boron nitride | 5.0 |
| (6) titanium dioxide | 5.0 |
| (7) iron oxide | 3.0 |
| (8) zinc stearate | 5.0 |
| (9) ACES | 1.0 |
| (10) CAPS | 1.0 |
| (11) CAPSO | 1.0 |
| (12) liquid petrolatum | balance |
| (13) glycerine triisooctanic acid | 15.0 |
| (14) sorbitan sesqui-oleic acid | 1.5 |
| (15) preservative | appropriate amount |
| (16) fragrance | appropriate amount |

(Preparation Method)

(1) to (8) were mixed and ground. Other compounds (9) to (16) are mixed and added, then stirred to mix, and formed by a container to yield a solid foundation.

Example 89

Water-In-Oil Emulsion Type Foundation

| Prescription - Blend Ratio (% by mass) | |
|---|---|
| (1) spherical nylon | 10.0 |
| (2) porous unhydride silicic acid powder | 8.0 |
| (3) mica titanium | 2.0 |
| (4) silicon-processed sericite | 2.0 |
| (5) silicon-processed mica | 12.0 |
| (6) silicon-processed titanium dioxide | 5.0 |
| (7) silicon-processed iron oxide | 2.0 |
| (8) ion-exchanged water | balance |
| (9) ACES | 0.5 |
| (10) CAPS | 2.0 |
| (11) CAPSO | 2.0 |
| (12) decamethylcyclopentane siloxane | 18.0 |
| (13) dimethylpolysiloxane | 5.0 |
| (14) squalane | 1.0 |
| (15) POE denatured dimethylpolysiloxane | 2.0 |
| (16) preservative | appropriate amount |
| (17) fragrance | appropriate amount |

(Preparation Method)

Compounds (9) to (17) were mixed to homogeneously dissolved, then (1) to (7) having mixed and ground were added thereto to be dispersed. This suspension was added with (8) to emulsify, then fill in a bottle to yield a water-in-oil emulsion type foundation.

Figure 1:
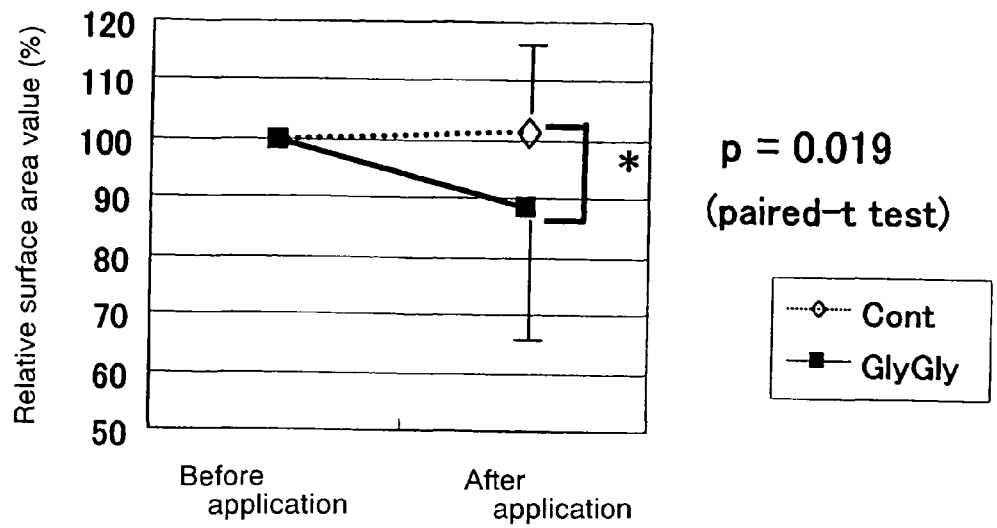
FIG. 1 is a schematic diagram showing the effect on the cheek pore surface area by applying glycylglycine.
Figure 2:
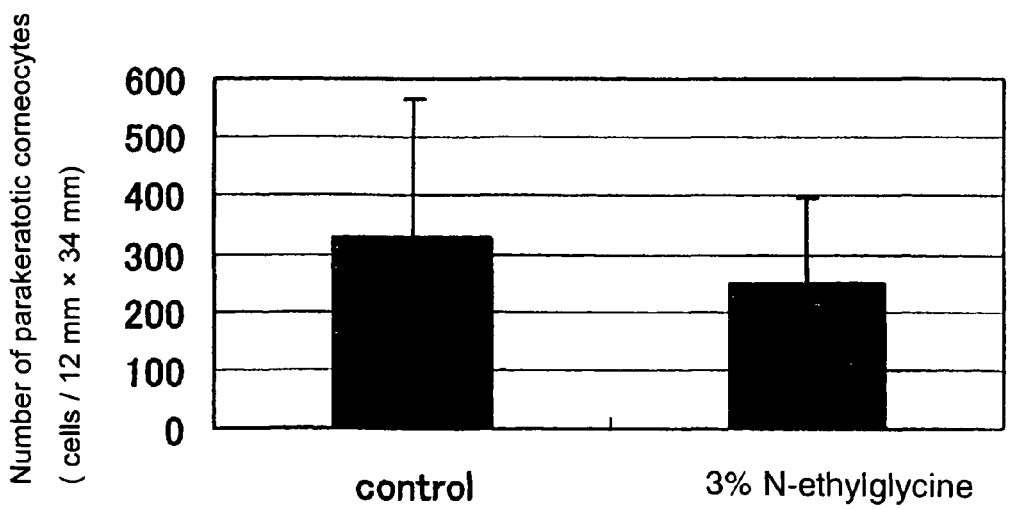
FIG. 2 is a schematic diagram showing the number of parakeratotic corneocytes after the application of N-ethylglycine 3 weight % solution and a control (ethanol 15 weight % solution)
Figure 3:
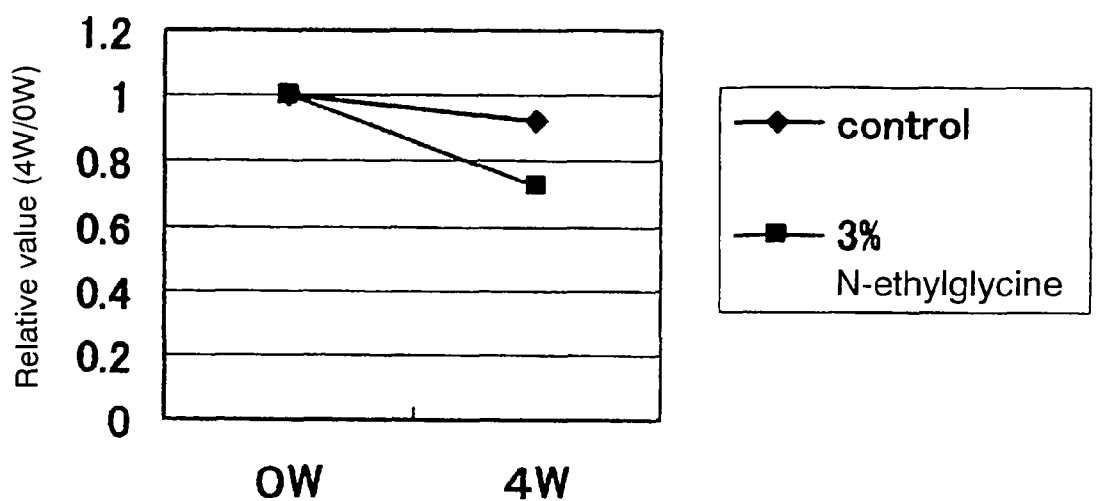
FIG. 3 is a schematic diagram showing the (relative value) amount of change of pore surface area by the analysis of replicas obtained before and after the application of N-ethylglycine 3 weight % solution and a control (ethanol 15 weight % solution).

What is claimed is:

1. A method of shrinking a skin pore comprising:
using glycylglycine in order to shrink the skin pore.

2. The method of claim 1, comprising applying an effective amount of the glycylglycine to an external surface of skin.

3. The method of claim 2, comprising forming a skin preparation comprising the effective amount of the glycylglycine and applying the skin preparation to an external surface of skin.

* * * * *